(12) United States Patent
Wilkinson et al.

(10) Patent No.: US 7,708,697 B2
(45) Date of Patent: May 4, 2010

(54) METHOD AND APPARATUS FOR DETERMINING CONDITIONS OF BIOLOGICAL TISSUES

(75) Inventors: Malcolm Howard Wilkinson, Forest Hill (AU); Clive Andrew Ramsden, Cheltenham (AU); Philip John Berger, Carlton (AU); Peter Camilleri, Springvale (AU); Jacqueline Anne Wilson, Fernlee Gully (AU); Frank Samuhel, Dromana (AU)

(73) Assignee: Pulmosonix Pty Ltd, Elsternwick, Vic (AU)

( * ) Notice: Subject to any disclaimer, the term of this patent is extended or adjusted under 35 U.S.C. 154(b) by 821 days.

(21) Appl. No.: 11/107,999

(22) Filed: Apr. 15, 2005

(65) Prior Publication Data

US 2006/0037615 A1    Feb. 23, 2006

Related U.S. Application Data

(63) Continuation-in-part of application No. 10/272,494, filed on Oct. 15, 2002, now Pat. No. 7,347,824, which is a continuation of application No. PCT/AU01/00465, filed on Apr. 20, 2001.

(60) Provisional application No. 60/664,011, filed on Mar. 22, 2005.

(30) Foreign Application Priority Data

Apr. 20, 2000  (AU) .................................... PQ7040
Apr. 10, 2001  (AU) .................................... PR4333

(51) Int. Cl.
*A61B 5/08*    (2006.01)

(52) U.S. Cl. ..................................... 600/533; 600/529

(58) Field of Classification Search ................. 600/533
See application file for complete search history.

(56) References Cited

U.S. PATENT DOCUMENTS 3,990,435 A    11/1976    Murphy (Continued)

FOREIGN PATENT DOCUMENTS

FR    2 672 793    8/1992

(Continued)

OTHER PUBLICATIONS

Pseudo-noise (PN). (2001). In Hargrave's Communications Dictionary, Wiley. Retrieved Dec. 5, 2007, from http://www.credoreference.com/entry/2723988.*

(Continued)

*Primary Examiner*—Patricia C Mallari
(74) *Attorney, Agent, or Firm*—Ladas & Parry LLP

(57) ABSTRACT

Airway monitoring apparatus 30 includes a driver 6 for applying sound in the audible frequency range to the airway of a subject and a detector 7 for monitoring the response of the airway, e.g. by detecting transmitted sound signal components and/or reflected sound signal components. Variations in the detected sound signal, e.g. energy, due to attenuation of the signal, give an indication of the state of the airway, e.g. airway patency, and can be used to monitor sleep-disordered breathing events, such as apnea and hypopnea, and to provide a breathing event index, e.g. AHI. The apparatus may provide servo-control for a respiratory assist device, such as a positive airway pressure device, so as to provide an appropriate pressure level setting. It may allow for home use of such devices and for home titration. It may also assist in discriminating central and obstructive breathing events, and in providing a measure of airway resistance.

47 Claims, 13 Drawing Sheets

U.S. PATENT DOCUMENTS

| | | | |
|---|---|---|---|
| 4,094,304 A | 6/1978 | Wright, Jr. | |
| 4,197,856 A | 4/1980 | Northrop | |
| 4,326,416 A | 4/1982 | Fredberg | |
| 4,672,977 A | 6/1987 | Kroll | |
| 4,830,015 A | 5/1989 | Okazaki | |
| 4,982,738 A | 1/1991 | Griebel | |
| 5,165,417 A | 11/1992 | Murphy, Jr. | |
| 5,239,997 A | 8/1993 | Guarino et al. | |
| 5,259,373 A | 11/1993 | Gruenke et al. | |
| 5,311,875 A | 5/1994 | Stasz | |
| 5,316,002 A | 5/1994 | Jackson et al. | |
| 5,318,038 A * | 6/1994 | Jackson et al. | 600/533 |
| 5,361,767 A | 11/1994 | Yukov | |
| 5,417,215 A | 5/1995 | Evans et al. | |
| 5,485,841 A | 1/1996 | Watkin et al. | |
| 5,588,439 A | 12/1996 | Hollub | |
| 5,620,004 A | 4/1997 | Johansen | |
| 5,666,960 A | 9/1997 | Fredberg et al. | |
| 5,746,699 A | 5/1998 | Fredberg et al. | |
| 5,844,997 A | 12/1998 | Murphy, Jr. | |
| 5,882,314 A | 3/1999 | Fredberg et al. | |
| 5,919,139 A | 7/1999 | Lin | |
| 6,045,514 A | 4/2000 | Raviv et al. | |
| 6,139,505 A | 10/2000 | Murphy | |
| 6,142,952 A * | 11/2000 | Behbehani et al. | 600/533 |
| 6,213,955 B1 | 4/2001 | Karakasoglu et al. | |
| 6,241,683 B1 | 6/2001 | Macklem et al. | |
| 6,261,238 B1 | 7/2001 | Gavriely | |
| 6,383,142 B1 * | 5/2002 | Gavriely | 600/529 |
| 6,394,967 B1 | 5/2002 | Murphy | |
| 6,440,083 B1 | 8/2002 | Fredberg et al. | |
| 6,443,907 B1 * | 9/2002 | Mansy et al. | 600/529 |
| 6,454,724 B1 | 9/2002 | Greene | |
| 6,491,641 B1 | 12/2002 | Rasmussen | |
| 6,517,497 B2 | 2/2003 | Rymut et al. | |
| 6,811,538 B2 | 11/2004 | Westbrook et al. | |
| 2002/0002327 A1* | 1/2002 | Grant et al. | 600/324 |
| 2002/0014235 A1 | 2/2002 | Rogers et al. | |
| 2002/0072685 A1 | 6/2002 | Rymut et al. | |
| 2002/0183642 A1 | 12/2002 | Murphy | |
| 2002/0193697 A1 | 12/2002 | Cho et al. | |
| 2003/0045806 A1 | 3/2003 | Brydon | |
| 2004/0010202 A1 | 1/2004 | Nakatani et al. | |
| 2004/0059240 A1 | 3/2004 | Cho et al. | |
| 2004/0069304 A1 | 4/2004 | Jam | |
| 2004/0236241 A1 | 11/2004 | Murphy | |
| 2004/0254493 A1 | 12/2004 | Chervin et al. | |
| 2005/0005935 A1 | 1/2005 | Gradon | |
| 2005/0020932 A1 | 1/2005 | Haberland et al. | |
| 2005/0027207 A1 | 2/2005 | Westbrook et al. | |
| 2005/0043645 A1 | 2/2005 | Ono et al. | |

FOREIGN PATENT DOCUMENTS

| | | |
|---|---|---|
| WO | 97/29687 | 8/1997 |
| WO | 99/32035 | 7/1999 |
| WO | 00/33735 | 6/2000 |
| WO | 02/13677 | 2/2002 |
| WO | 02/13697 | 2/2002 |
| WO | 02/43579 | 6/2002 |
| WO | 02/065901 | 8/2002 |
| WO | 03/024335 | 3/2003 |
| WO | 03/061471 | 7/2003 |
| WO | 03/063701 | 8/2003 |
| WO | 03/075739 | 9/2003 |
| WO | 03/092493 | 11/2003 |

OTHER PUBLICATIONS

"Pseudorandom noise" from Wikipedia, the free encyclopedia. Retrieved Dec. 5, 2007 from http://en.wikipedia.org/wiki/Pseudorandom_noise.*

English Abstract of FR 2 672 793 Dated Aug. 21, 1992.

Murphy, R., et al. "Sound Speed in the Lung Measured by Sound Injection into Supraclavicular Space." *European Respiratory Society Congress* (2002) abstract.

Paciej, R., et al. "Transpulmonary Speed of Sound Input into Supraclavicular Space." *J. Appl. Physiol* (1994) vol. 94, pp. 604-611.

Bergstresser, T., et al. "Sound Transmission in the Lung as a Function of Lung Volume." *J. Appl. Physiol.* (2002) vol. 93, pp. 667-674.

Dalmay et al. "Acoustic Properties of the Normal Chest" *European Respiratory Journal* (1995) vol. 8, pp. 1761-1769.

Pasterkamp et al. "Respiratory Sounds—Advances Beyond the Stethoscope" *American Journal of Respiratory and Critical Care Medicine* (1997) vol. 156, pp. 975-985.

Karnath et al. "Pulmonary Auscultation" *Hospital Physician* (2002) pp. 22-26.

Leung et al. "Sound Transmission Between 50 and 600 Hz in Excised Pig Lungs Filled with Air and Helium" *Journal of Applied Physiology* (2000) vol. 89, Issue 6, pp. 2472-2482.

Wodicka et al. "Spectral Characteristics of Sound Transmission in the Human Respiratory System" *IEEE Transactions on Biomedical Engineering* (1990) vol. 37, No. 12, pp. 1130-1135.

Leung et al. "Sound Transmission Through Normal and Diseased Human Lungs" *Engineering Science and Education Journal* (1996) pp. 25-31.

Wodicka et al. "Phase Delay of Pulmonary Acoustic Transmission from Trachea to Chest Wall" *IEEE Transactions on Biomedical Engineering* (1992) vol. 39, No. 10, pp. 1053-1059.

Mahagnah et al. "Gas Density Does Not Affect Pulmonary Acoustic Transmission in Normal Men" *Journal of Applied Physiology* (1995) vol. 78, Issue 3, pp. 928-937.

Pohlmann et al. "Effect of Changes in Lung Volume on Acoustic Transmission through the Human Respiratory System" *Physiological Measurement* (2001) vol. 22, pp. 233-243.

Huang et al. "A New Nasal Acoustic Reflection Technique to Estimate Pharyngeal Cross-Sectional Area During Sleep" *Journal of Applied Physiology* (2000) vol. 88, pp. 1457-1466.

Poort et al. "Airway Area by Acoustic Reflection: A Corrected Derivation for the Two-Microphone Method" *Journal of Biomechanical Engineering* (1999) vol. 121, pp. 663-665.

Marshall et al. "Acoustic Reflectometry for Airway Measurements in Man: Implementation and Validation" *Physiological Measurement* (1993) vol. 14, pp. 157-169.

Louis et al. "Airway Area by Acoustic Reflection: The Two-Microphone Method" *Journal of Biomechanical Engineering* (1993) vol. 115, pp. 278-285.

Rubinstein et al. "Effect of Mouthpiece, Noseclips, and Head Position on Airway Area Measured by Acoustic Reflections" *The American Physiological Society* (1987) pp. 1469-1474.

Brooks et al. "Reproducibility and Accuracy of Airway Area by Acoustic Reflection" *Journal of Applied Physiology* (1986) vol. 57, pp. 777-787.

Fredberg et al. "Airway Area by Acoustic Reflections Measured at the Mouth" *Journal of Applied Physiology* (1980) vol. 48, pp. 749-758.

Sidell et al. "Noninvasive Inference of Airway Network Geometry from Broadband Lung Reflection Data" *Journal of Biomechanical Engineering* (1978) vol. 100, pp. 131-138.

Jackson et al. "Airway Geometry by Analysis of Acoustic Pulse Response Measurements" *Journal of Applied Physiology* (1977) vol. 43, pp. 523-536.

Ware et al. "Continuous and Discrete Inverse-Scattering Problems in a Stratified Elastic Medium-I. Plane Waves at Normal Incidence" *The Journal of Acoustical Society of America* (1969) vol. 45, No. 4, pp. 911-921.

Faber et al. "Flextube Reflectometry for Localization of Upper Airway Narrowing—A Preliminary Study in Models and Awake Subjects" *Respiratory Medicine* (2001) vol. 95, pp. 631-638.

Carrive et al. "Biophony: An Open System to Measure the Airway Area by Acoustic Reflection" *18th Annual International Conference of the IEEE Engineering in Medicine and Biology Society* (1996) pp. 125-126.

Murphy et al. "Spectral Characteristics of Lung Sounds in Patients with Chronic Obstructive Lung Disease" Faulkner Hospital, Boston, MA, presented at ATS 2004 (2002) one page.

Murphy et al. "Inhomogeneity of the Timing of Lung Sounds in Patients with Chronic Obstructive Lung Disease" Faulkner Hospital, Boston, MA, presented at ATS 2002 (2002) one page.

Murphy et al. "Inhomogeneity of the Timing of Lung Sounds in Patients with Chronic Obstructive Lung Disease" Faulkner Hospital, Boston, MA, presented at ATS 2002 (2002) one page.

* cited by examiner

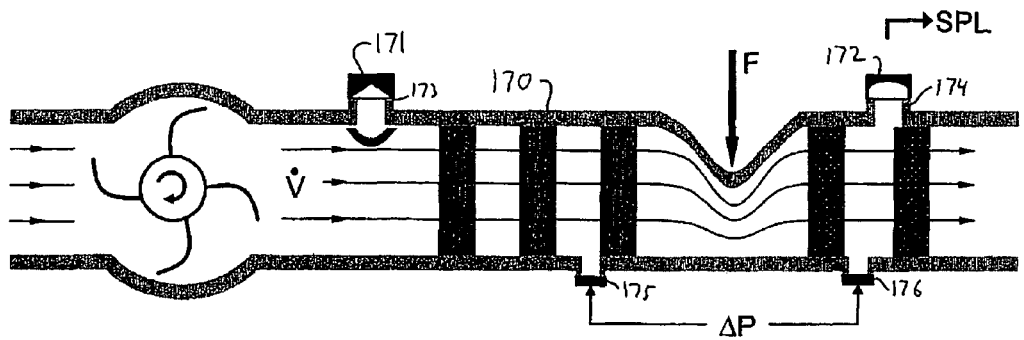
Fig. 23
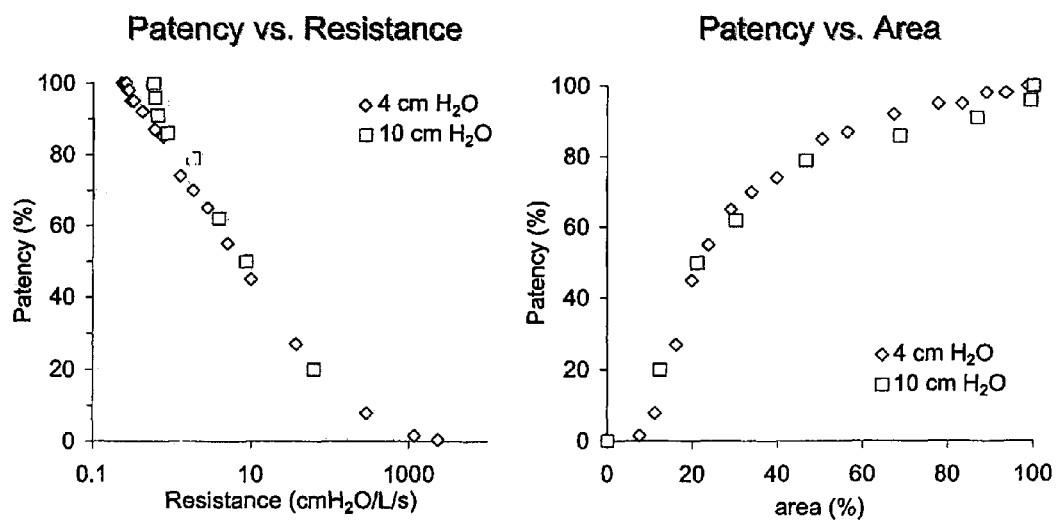
Fig. 24
Fig. 25

US 7,708,697 B2

METHOD AND APPARATUS FOR DETERMINING CONDITIONS OF BIOLOGICAL TISSUES

The present application is a continuation-in-part of U.S. Ser. No. 10/272,494 entitled "Method and Apparatus for Determining Conditions of Biological Tissues" and filed on 15 Oct. 2002 now U.S. Pat. No. 7,347,824, which is a continuation of International Patent Application No. PCT/AU01/00465 entitled "Method and Apparatus for Determining Conditions of Biological Tissues" filed on 20 Apr. 2001. The present application also claims the benefit of U.S. Provisional Patent Application No. 60/664,011 entitled "Apparatus, Systems and Methods for Monitoring Airway Patency" filed on 22 Mar. 2005. The contents of each of these applications are incorporated by reference in their entirety in the present application.

The present invention relates to a method of determining characteristics of biological tissues in humans and animals. In particular, it relates to determining the characteristics of tissues such as the lungs and airways by introducing a sound to the tissue, and recording the sound. The invention further includes apparatus capable of determining such characteristics.

The present invention relates to the determination of airway states, to the determination of airway patency and to the degree of airway patency, to the provision of breathing indices, to the discrimination of central and obstructive breathing events, to the control of respiratory assist devices, and to the diagnosis, assessment and treatment of respiratory conditions.

BACKGROUND OF THE INVENTION

Non-invasive determination of the condition of biological tissues is useful in particular where the patient is unable to co-operate or the tissue is inaccessible for easy monitoring.

Techniques presently used in determining the characteristics of biological tissues include x-rays, magnetic resonance imaging (MRI) and radio-isotopic imaging. These are generally expensive and involve some degree of risk which is usually associated with the use of X-rays, radioactive materials or gamma-ray emission. Furthermore, these techniques are generally complicated and require equipment which is bulky and expensive to install and, in most cases, cannot be taken to the bedside to assess biological tissues in patients whose illness prevents them being moved. The present invention provides methods and apparatus which alleviate these difficulties, providing non-invasive, cost-effective and ambulatory means for assessing and monitoring the condition of biological tissues in humans and animals alike.

Sound waves, particularly in the ultra-sound range have been used to monitor and observe the condition of patients or of selected tissues, such as the placenta or fetus. However, the process requires sophisticated and sometimes expensive technology and cannot be used in tissues in which there is a substantial quantity of gas, such as the lung.

Every year in Australia about 5000 newborn infants require a period of intensive care (ANZNN Annual Report, 1996-1997). Respiratory failure is the most common problem requiring support and is usually treated with a period of mechanical ventilation. Over the last decade the mortality of infants suffering respiratory failure has shown an impressive decline, attributable at least in part to improved techniques used in mechanical ventilation, and the introduction of surfactant replacement therapy (Jobe, 1993). The vast majority of infants now survive initial acute respiratory illness, but lung injury associated with mechanical ventilation causes many infants to develop 'chronic lung disease'. Chronic lung disease is characterised by persisting inflammatory and fibrotic changes, and causes over 90% of surviving infants born at less than 28 weeks gestation, and 30% of those of 28-31 weeks gestation, to be dependent on supplementary oxygen at 28 days of age. Of these, over half still require supplementary oxygen when they have reached a post-menstrual age of 36 weeks gestation (ANZNN Annual report, 1996-1997). Assistance with continuous positive airway pressure (CPAP) or artificial ventilation is also commonly required.

Historically, barotrauma and oxygen toxicity have been considered to be the primary culprits in the aetiology of chronic lung disease (Northway et al, 1967; Taghizadeh & Reynolds, 1976). However, trials of new strategies in mechanical ventilation which were expected to reduce barotrauma and/or exposure to oxygen have often had disappointingly little impact on the incidence of chronic lung disease (HIFI Study Group, 1989; Bernstein et al, 1996; Baumer, 2000). Comparison of strategies of conventional mechanical ventilation in animals (Dreyfuss et al, 1985) have indicated that high lung volumes may be more damaging than high intrapulmonary pressures, and has led to the concept of 'volutrauma' due to over-inflation of the lung. At the same time, experience with high frequency oscillatory ventilation (HFOV) has indicated that avoidance of under-inflation may be equally important. HFOV offers the potential to reduce lung injury by employing exceptionally small tidal volumes which are delivered at a very high frequency. However, this technique fails to confer benefit if the average lung volume is low (HIFI Study Group, 1989), yet it appears to be successful if a normal volume is maintained (McCulloch et al, 1988; Gerstmann et al, 1996). This highlights the importance of keeping the atelectasis-prone lung 'open' (Froese, 1989). Evidence of this kind has led to the concept that a 'safe window' of lung volume exists within which the likelihood of lung injury can be minimised. The key to preventing lung injury may lie in maintaining lung volume within that safe window thereby avoiding either repetitive over-inflation or sustained atelectasis. (See FIG. 1).

Attempts to maintain an optimal lung volume in the clinical setting are frustrated by a lack of suitable methods by which the degree of lung inflation can be monitored. In current practice, evaluation of oxygen requirements and radiological examination of the lungs are the principal techniques employed. However, oxygen requirements may be influenced by factors other than lung volume (for example intra- or extracardiac right to left shunting), and the hazards of radiation exposure prevent radiological examination being performed with the frequency required.

Monitoring of infants during mechanical ventilation has been significantly improved over the last decade by the incorporation of a pneumotachograph or hot-wire anemometer into the design of many neonatal ventilators. Although this provides a valuable tool for monitoring tidal volume and compliance, it gives only the most indirect indication (from the shape of the pressure-volume curve) of whether that tidal volume is being delivered in a setting of under-inflation, optimal inflation, or over-inflation. Furthermore, while absolute lung gas volume can be measured using 'gold-standard' techniques of Nitrogen ($N_2$) washout or Helium (He) dilution, these are impractical for routine clinical use.

Even when lung volume is maintained in the "safe window", changes in the lung condition may manifest due to the generally damaged or underdeveloped condition of the lung. Fluid and blood may accumulate in the lung, posing additional threats to the patient. Evaluation with a stethoscope of audible sounds which originate from within the lung (breath sounds) or are introduced into the lung (by percussion, or as vocal sounds) forms an essential part of any routine medical examination. However, in the sick newborn, the infant's small size, inability to co-operate and the presence of background noise greatly limits the value of such techniques.

Whilst determining and monitoring lung condition in newborn babies is difficult, determining lung condition in adults can be equally challenging, particularly if a patient is unconscious or unable to cooperate. This places a further limitation on the presently available techniques for monitoring lung condition. Therefore, a clear need exists for a simple, non-invasive and convenient method by which the condition of the lung can be closely monitored in the clinical setting.

Similarly, there is a need for simple, non-invasive and convenient methods and apparatus for determining the condition of other biological tissues which may be prone to changes in their characteristics, through pathology or otherwise.

For example, it would be very useful to be able to monitor the state of the airways. This can be especially useful for example in the determination of airway patency and in the determination of sleep-disordered breathing.

Sleep-disordered breathing is an increasingly recognised clinical problem, with severe obstructive sleep apnea affecting an estimated 5% of adults and 2% of infants.

In sleep-disordered breathing a reduction in airflow to the lungs may result in reduced blood oxygen levels (hypoxemia) and arousal from sleep. This airflow reduction and arousal can occur many times a night, and can have a number of adverse effects, including excessive daytime sleepiness and an increased incidence of cardiovascular disease and stroke.

In obstructive sleep apnea, a patient's upper airway may be prone to collapse during sleep, thereby causing an obstruction and hypoxemia. This in turn causes the patient to enter a waking state for a short time period. The airway is then re-opened, airflow is re-established, and the patient immediately returns to sleep. This sequence of events may repeat many times throughout the night.

Apnea is generally characterised by a cessation of airflow for 10 or more seconds, and may be classified as obstructive apnea (caused by a blockage of the airway), central apnea (e.g. lack of breathing effort caused by an unstable respiratory control system or as a result of a neurological condition), or mixed apnea (a combination of both).

Sleep-disordered breathing may also relate to hypopnea, which is generally characterised as a reduction of airflow, and for example may be due to an airway that is partially obstructed or may be of central origin, resulting from a reduced output from the respiratory centre in the brain stem. It may also relate to other conditions, such as Upper Airway Resistance Syndrome (UARS), in which there is a reduction in airflow involving arousal, but there may be no significant lowering of blood oxygen levels.

At present, the diagnosis of sleep-disordered breathing is difficult and is generally carried out by a polysomnography test, in which a number of physiological variables of a patient are monitored overnight in a sleep laboratory. This must be followed by a detailed analysis of the resulting data by an experienced sleep scientist, and requires a rigorous comparison of multiple traces. It is expensive, time-consuming and subject to inaccuracies.

Other methods of determining airway obstruction also exist. For example, an oesophageal balloon catheter may be used to measure oesophageal pressure, and, in association with inspiratory airflow, this may be used to calculate upper airway resistance. Such methods are however too invasive for routine clinical use.

The present invention, in its various aspects, aims to provide new and useful apparatus, systems and methods for monitoring the state of an airway and for monitoring patency.

SUMMARY OF THE INVENTION

In a first aspect of the present invention there is provided a method of determining characteristics of biological tissue in situ, including:
  introducing a sound to the tissue at first position;
  detecting the sound at another position spaced from the first position after it has travelled through the tissue;
  calculating the velocity and attenuation of sound that has travelled through the tissue from the first position to another position; and
  correlating the velocity and attenuation of the detected sound to characteristics of the biological tissue.

In another aspect of the present invention there is provided an apparatus for determining characteristics of biological tissues, the apparatus including:
  a sound generating device which generates a sound;
  a recording device which records the sound after it has travelled from one position of the biological tissue, through the tissue and to another position of the tissue;
  an analysis device which calculates the velocity with which the sound travels through the tissue, and its attenuation, and which can preferably perform spectral analysis on the data recorded.

In a preferred aspect of the present invention, there is provided a method of determining a state of the upper airways in a respiratory tract in a patient in situ, said method including:
  introducing a sound at first position in the upper airways;
  detecting the sound after it has travelled through the upper airways at another position spaced from the first position;
  calculating the velocity and attenuation of the sound that has travelled through the upper airways from the first position to another position; and
  correlating the velocity and attenuation of the sound to a state of the upper airways.

This method is particularly useful for monitoring for sleep apnea.

In one aspect, the present invention provides apparatus for monitoring airway patency, the apparatus including:
  a sound generator for applying a sound signal in the audible frequency spectrum to an airway;
  a detector for detecting the sound signal after it has travelled through at least a portion of the airway; and
  an analyser for monitoring airway patency based on variations in the detected sound signal.

Sound in the audible frequency spectrum relates to e.g. sound waves of a frequency from about 20 Hz to about 20 kHz.

The present invention provides a simple, non-invasive and effective method of determining airway patency. The apparatus need not require specialist skills to use, or require expensive or intrusive equipment to implement, and need not inconvenience the patient under examination.

The present invention may be used to determine the state of the upper airways, and may be used to indicate conditions such as complete or partial obstruction of the airways.

The apparatus may detect sound transmitted through an airway portion or sound reflected back from an airway portion. The properties of the detected sound signal may be monitored in order to determine whether the airway is open or not and/or to determine the degree of patency.

For both transmitted and reflected signal detection, the detected signal properties relate to the input signal through a complex combination of attenuation, transmission, refraction and reflection from various sites along the airway.

For a transmitted signal an increase in attenuation would be indicative of a reduction in patency, whilst a small degree of attenuation would indicate a clear airway (there will always be some degree of attenuation in the sound signal as it travels through the airways). For a reflected signal the complex interaction between transmitted and reflected paths would represent the state of the airway and changes to this response would be indicative of a change in patency.

It will be noted that the detected signal may often be an indirect measurement, e.g. taken on the body of the patient, which detects the signal after it has passed through the relevant portion of the airway and coupled to the detector through the body tissue.

The patency information may be used by itself to determine the degree of airway obstruction, e.g. to establish the existence of obstructive apnea or hypopnea or the like, and/or may be used with other data, such as airflow, to distinguish obstructive apnea from central apnea. Combined data may be used to provide a breathing index, such as an Apnea Index (AI), an Apnea Hypopnea Index (AHI) or a Respiratory Disturbance Index (RDI).

The present invention may also be used in a system for assisting in sleep disordered breathing treatments. For example, CPAP (continuous positive airway pressure) provides continuous positive pressure airflow to a patient during sleep, so as to splint the airways open, and the present invention may be used as a servo-control for devices such as CPAP equipment or variants thereof, e.g. BIPAP devices (having different inhalation and exhalation pressures) and APAP devices (having varying pressures). It may provide for auto-titration of such devices, so as to ensure the correct pressure is set for a particular patient. The present invention may also be used to servo-control respiratory assist devices in general.

The sound signal may be applied through one of the nares, both of the nares, the mouth, or the mouth and the nares, and may be applied through a face mask, a nose mask, a mouth mask, nasal plugs or nasal cannulas.

For reflective signal detection, the sound signal may be applied to one of the nares and detected from the other, applied to both nares and detected from both, applied orally and detected orally, or applied to the nose and/or mouth and detected in the other or both. The detectors may be provided proximal to the nose or mouth, e.g. in a mask or in a nasal plug or cannula prong. They may also be provided remote from the nose or mouth e.g. in a respirator line or in a cannula line.

For transmitted signal detection, the detector in one form is positioned on the skin surface at the base of the throat, e.g. in the region of the supra-sternal notch, and may be sized to fit within this notch. This position is advantageous for monitoring the sound level in the trachea, as the amount of tissue at the notch is suitably low so as to provide a good detection signal with little attenuation. Other sensor positions are also possible, e.g. other regions of the neck, on the chest or back, or on the abdomen. These other positions, e.g. chest, back or abdomen may be especially useful for neonates.

The system may include more than one detector. Their outputs may be used to provide a more reliable output, e.g. by averaging the outputs or by taking the signal that is most optimal, e.g. the greater of the outputs. The detected signals could also be added to or subtracted from one another, or the signals could be processed independently. They may be used to determine patency in different portions of the airway, and a combination of transmission and reflection signal detectors may be used.

The applied sound signal may be a single tone or a combination of tones. In one embodiment, the input signal is in the form of random noise, or a tone or tones masked by random noise. This has the benefit that the applied sound does not appear intrusive or disconcerting to the patient, which may be an important consideration for the system's implementation.

The signal is preferably pseudo-random noise or a noise sequence with a known structure. It is preferably of the form of white noise. It may for example take the form of Gaussian white noise or band-limited white noise. In one preferred embodiment, MLS (maximum length sequence) noise is utilised and e.g. band-limited white noise may be derived from this.

The sound generator may generate sound signals based on a repeating noise signal sequence, the length of the repeated sequence being such that the repetition is substantially unperceived by the subject whose airway is being monitored. This repeated sequence may be divided into a plurality of signal packets to allow for processing of the detected signal at a rate higher than the repeated sequence length. In this manner, patency updates are not limited by the length of the repeat sequence, and, e.g. a patency determination may be made over one or more of the packets. In a preferred embodiment, each packet is normalised. For example, each packet is amplitude normalised, e.g. using an RMS value, so that each has the same mean value. Normalisation can reduce fluctuations in the response signal by adjusting the packets so that they each have the same average energy.

The detected sound signal may be analysed directly, e.g. in respect of attenuation. Preferably, however, the analyser correlates the detected sound signal with a reference signal, e.g. to determine the degree of attenuation. Preferably, the correlation is a cross-correlation. In one embodiment, the reference signal comprises the pseudo-random noise signal used to generate the applied sound signal. In another embodiment, the reference signal comprises a sound signal detected at the sound generator, and, in another embodiment, the reference signal is derived from a sound signal detected in proximity to the patient. The reference signal may for example be determined from the output of a further sound sensor.

Correlation helps to reduce errors introduced by extraneous noise, which can be significant due to the noisy environment in which the present signals are detected, e.g. due to respiratory sounds and external sounds such as in a doctor's surgery or hospital, where many sources of extraneous audible signals may be present.

The output of the correlator provides an impulse response that is not only for the airway, but is a system response for a combination of the airway and the associated measurement apparatus, including for example the signal filtering. Although the system impulse response is not the actual impulse response of the airway by itself, the airway is the significant variable in the combination, and therefore changes in the detected overall response can be associated with changes in the airway itself. Also, suitable calibration of the signal, e.g. with open and forced closure states (e.g. through a sustained swallow), can provide appropriate airway patency values.

The analyser may determine a peak value in a signal response to determine patency. For example, the analyser may determine the position of a peak in an impulse response and monitor the strength of the impulse response at that point in order to determine patency. Alternatively, the analyser may track a peak in the impulse response over time, and monitor the strength of the peak in order to determine the degree of patency.

Alternatives to these methods are also possible. For example, multiple peaks of the impulse response may be used. Also, a Fast Fourier Transform (FFT) may be applied to the impulse response in order to provide the airway frequency response, and patency may be determined from a characteristic of this response, e.g. the amplitude or amplitudes of one or more of the various frequency components of the signal. The RMS value of the FFT may also be used to determine patency. In further embodiments, an RMS, mean or integrated value of the detected signal or the impulse or frequency response may be used to give a patency measure.

In the case of a reflected signal, the analyser may also determine patency based on a variation in the temporal or frequency profile of the detected signal, e.g. an energy distribution of the signal. The apparatus may for example compare characteristics of the detected signal in at least two selected time windows to determine patency, and for example may compare a part of the signal associated with the airway above a blockage and a part of the signal associated with the airway below the blockage. It may compare sub-glottal response characteristics (e.g. energy) to supra-glottal response characteristics to determine patency.

The applied sound signal may have frequencies and bandwidths chosen to ensure a good response and robustness against noise, without causing discomfort to a patient under examination.

The applied sound signal may be based on a frequency characteristic of the patient airway, e.g. a resonant frequency of the airway. The response may be chosen as one that is substantially stable during open and closed mouth events.

The apparatus may tune the applied sound signal to the patient so as to provide an optimum response. It may for example include a tunable bandpass filter that provides an optimum response signal. The filter may be tuned so as to provide a band of frequencies centred on a particular airway resonance, which may differ from patient to patient. In one embodiment, the applied sound signal is tuned so as to ensure that a characteristic of the detected signal, e.g. a characteristic of the impulse response, such as a main peak thereof, is maximised.

The apparatus may include means for monitoring the signal level of the detected signal and for rejecting signal data above a threshold value. This can help to prevent erroneous determination of patency, e.g. a snore may produce a high output from the detector and could result in an erroneous calculation of patency.

The threshold may be a set threshold and/or an adaptive threshold that changes its value based on the level of the detected signal. The adaptive threshold may be set to a value based on the RMS value of the detected signal, e.g. four times the RMS value. This helps to reduce the effects of large transient noise signals, whilst adjusting to continuous long-lasting changes in interfering background noise. Both a high set threshold and a lower adaptive threshold may be used.

When signal data are rejected, the apparatus may continue to output patency data based on previous valid patency data. In one preferred form, a predictive algorithm may be provided in order to estimate patency for the time that the blanker is in operation. This estimation may be based on weighted previous patency data.

Where the detected sound signal is divided into a plurality of data packets, each packet being used to determine a patency value, and when a packet includes sampled data above the threshold value, the data from the packet may be rejected. Alternatively, when a detected data sample of a packet is above a threshold value, the detected data sample may be adjusted to a lower value, in which case, the average patency value based on an adjusted data packet may be adjusted to compensate for the adjusted data samples. For example, the patency value may be increased based on the amount of modified data in the sample, so that if 30% of the data in a packet are modified, e.g. reduced to zero amplitude, the calculated average patency value corresponding to the packet may be increased by 30%.

The apparatus may include means for invoking a frequency selective reduction of interfering signals by determining the fast Fourier transform of the detected sound signal and for attenuating frequency components that exceed a threshold value, e.g. a fixed threshold or a threshold based on frequency coefficients of the applied sound signal, e.g. as determined by the filter coefficients of the signal's FFT. The inverse fast Fourier transform may then be used to reconstruct the detected signal.

The apparatus may determine the location of an obstruction based on the detected sound signal. It may for example do this based on time of flight information of reflected signals or by monitoring changes in the energy profile of the response, e.g. based on a comparison of at least two portions of the response signal one of which is positioned below the point of obstruction. It may utilise a change in the resonant frequencies to determine position, and may use frequency and phase change characteristics to determine position.

The apparatus may be used with other physiological parameters, such as cardiorespiratory parameters, including for example airflow, oxygen saturation and heart rate. The apparatus may for example include a nasal and/or oral pressure sensor, a mask pressure sensor, a nasal or oral thermistor and/or an in-line flow sensor.

The apparatus may discriminate between a centrally mediated event (caused by an unstable respiratory control system or as a result of a neurological condition), an obstructive breathing event (e.g. caused by total or partial collapse of the airway) and a mixed breathing event (a combination of central and obstructive events). The analyser may further discriminate between an apneic event and a hypopneic event based on the degree of patency of the airway and/or the reduction of airflow. It may also distinguish other states, e.g. events associated with Upper Airway Resistance Syndrome.

The analyser may for example determine an obstruction when patency is low, a partial obstruction when patency is reduced, an obstruction when patency is low and airflow has ceased, a partial obstruction when patency and airflow are reduced, a cessation or reduction of an obstruction when patency rises, a central apnea when patency is high and airflow has ceased, an obstructive apnea when patency is low and airflow has ceased, an obstructive hypopnea when patency and airflow are reduced, and a central hypopnea when patency remains constant and airflow is reduced.

The apparatus may issue an alarm when a prolonged respiratory event occurs e.g. when patency is below a threshold value. It may provide apparatus for the monitoring of sleep-disordered breathing, wherein sleep-disordered breathing is determined based on detected patency.

It may provide a sleep-disordered breathing index, and may include an index calculator for counting the number of breathing events that occur in a set time period based on at least the detected patency of the airway. These indices relate to the average number of respiratory events per hour, e.g. an apneic or hypopneic event, and the apparatus may discriminate and record these events over time to provide the desired index.

The present invention may provide respiratory assist apparatus, wherein a respiratory assist function is controlled based on detected patency, and may be used for controlling positive airway pressure apparatus.

The positive airway pressure apparatus may include continuous positive airway pressure (CPAP) apparatus as well as variants, such as bi-level positive airway pressure (Bi-PAP) apparatus, on-demand positive airway pressure devices (DPAP) and variable and auto-titrating positive airway pressure (APAP and VPAP) apparatus. It may also be used in ventilators and respiratory treatment and therapy devices in general.

The patency signal may be used to control the timing of respiratory assistance, e.g. when to apply a positive pressure, and the degree of respiratory assist, e.g. the level of positive pressure. For example, the detection of an obstruction or decrease in patency may cause a positive airway pressure device to begin or increase the applied pressure, whilst an increase in patency may cause the device to stop or reduce the applied pressure. Generally, for CPAP devices, there will always be a positive pressure, and it will be the degree of positive pressure that is changed based on the servo-control. It would be possible however to use devices that allow a patient to breathe ambient air when not requiring a positive pressure to splint the airway open, and in this case the servo-control may determine a stop/start of the positive pressure as well as pressure level.

The present invention facilitates auto-titration of the positive pressure by allowing for servo-control of the respiratory assist apparatus so that it uses the patency feedback to determine a suitable pressure level for a patient that will hold the patient's airway open. This pressure level may be determined once for a patient, and that value then used in future treatment, or may be calculated on an on-going/periodic basis, so that the pressure level is continually monitored and corrected.

The present invention may facilitate home diagnosis and home titration, without the need for expert intervention and without the need for expensive overnight sleep studies in sleep laboratories.

Although mainly discussed in relation to sleep-disordered breathing, the present invention has other applications also. For example, the apparatus may be used to monitor the airway patency of an infant or incapacitated or unresponsive adult, e.g. during anaesthesia. The apparatus may for example alarm when patency is lost.

The present invention may also provide a way to determine airway resistance wherein resistance is determined based on patency of the airway.

Viewed from another aspect, the present invention provides a method of monitoring airway patency, including the steps of applying a sound signal in the audible frequency spectrum to an airway, detecting the sound signal after it has travelled through the airway; and analysing the sound signal to monitor patency of the airway based on variations in the detected sound signal.

Viewed from another aspect, the present invention provides sleep-disordered breathing monitoring apparatus, including a sound generator for applying a sound signal in the audible frequency spectrum to the airway of the subject, a detector for detecting a response of the airway to the applied sound signal, and an analyser for determining the occurrence of a sleep-disordered breathing event based on the detected response.

Viewed from another aspect, the present invention provides a method of diagnosing sleep disordered breathing, including the steps of applying a sound signal in the audible frequency spectrum to an airway; detecting the sound signal after it has travelled through the airway; determining one or more physiological parameters e.g. cardiorespiratory parameters such as airflow or oxygen saturation; and analysing variations in the detected sound signal and said one or more physiological parameters to determine sleep-disordered breathing events.

Viewed from another aspect, the present invention provides respiratory assist apparatus, the apparatus including a sound generator for applying a sound signal in the audible frequency spectrum to the airway of the subject, a detector for detecting a response to the applied sound signal, and an analyser for determining the need for a respiratory assist action based on the detected response.

Viewed from another aspect, the present invention provides a method of titrating a positive airway pressure respiratory assist device, the method including the steps of applying positive pressure to an airway; applying a sound signal in the audible frequency spectrum to the airway; detecting a response to the sound signal; determining one or more physiological parameters, e.g. cardiorespiratory parameters such as oxygen saturation or airflow; and analysing variations in the detected sound signal and said one or more physiological parameters and varying the amount of positive pressure applied to the airway to provide a suitable level of positive pressure to the patient.

Viewed from another aspect, the present invention provides apparatus for determining a sleep-disordered breathing index, the apparatus including a sound generator for applying a sound signal in the audible frequency spectrum to the airway of a subject, a detector for detecting a response to the applied sound signal, and an analyser for determining the occurrence of a sleep-disordered breathing event based on the detected response and for determining a sleep-disordered breathing index based on the frequency of the determined events.

Viewed from another aspect, the present invention provides apparatus for determining airway resistance, the apparatus including a sound generator for applying a sound signal in the audible frequency spectrum to an airway; a detector for detecting a response to the applied sound signal; and an analyser for determining airway resistance based on the detected response.

Viewed from another aspect, the present invention provides apparatus for monitoring airway patency, the apparatus including a sound generator for applying a sound signal in the audible frequency spectrum to an airway, the sound signal being based on pseudo-random noise; a detector for detecting the sound signal after it has travelled through at least a portion of the airway; a cross-correlator for determining an impulse response based on the detected signal and a reference signal related to the applied sound signal; and an analyser for monitoring a patency state for the airway based on a variation in the impulse response caused by an interaction of the applied sound signal with a portion of the airway.

Viewed from another aspect, the present invention provides apparatus for monitoring airway patency, the apparatus including a sound generator for applying a sound signal in the audible frequency spectrum to at least a portion of an airway, the airway portion having an end nearest (proximal) to the sound generator and an end distal from the sound generator; a detector for detecting a resulting sound signal at said distal end of said airway portion; and an analyser for determining patency for the airway portion based on the detected signal.

Viewed from another aspect, the present invention provides apparatus for monitoring airway patency, the apparatus including a sound generator for applying a sound signal in the audible frequency spectrum to at least a portion of an airway, the airway portion having an end nearest (proximal) to the sound generator and an end distal from the sound generator; a detector for detecting a resulting sound signal at said proximal end of said airway portion, said sound signal including components of said applied sound signal that are reflected back to said proximal end of said airway; and an analyser for determining patency for the airway portion based on the detected signal.

Viewed from another aspect, the present invention provides apparatus for monitoring a state of an airway, the apparatus including a sound generator for applying a sound signal in the audible frequency spectrum to an airway; a detector for detecting the sound signal after it has travelled through at least a portion of the airway; and an analyser for monitoring the state of the airway based on variations in the detected sound signal.

BRIEF DESCRIPTION OF THE FIGURES

FIG. 23 is a schematic of an experimental set-up in which an upper airway obstruction is modeled by a rubber tube whose cross-sectional area can be progressively reduced and the associated airway resistance determined.

FIGS. 24 and 25 are graphs respectively of the relationship between airway resistance, cross-sectional area and patency determined from the experiment of FIG. 23.

DETAILED DESCRIPTION

Figure 1:
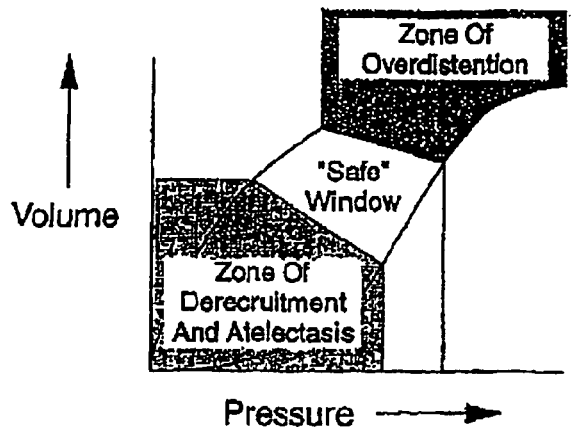
FIG. 1 shows a pressure-volume curve of a moderately diseased lung illustrating two hazardous regions of lung volume, and indicating an optimal "safe" window there between (from Froese, 1997).

Characteristics of biological tissues can be determined by measuring the velocity and attenuation of a sound as it propagates through the tissue. This can be achieved by introducing a sound to a particular location or position on the tissue, allowing the sound to propagate through the tissue and measuring the velocity and attenuation with which the sound travels from its source to its destination, wherein the destination includes a receiver which is spatially separated from the sound's source.

Characteristics of the biological tissue may include a feature of the tissue including but not limited to its make-up, volume, condition or position in the body.

Biological tissues may include any single tissue or a group of tissues making up an organ or part or region of the body. The tissue may comprise a homogeneous cellular material or it may be a composite structure such as that found in regions of the body including the thorax which for instance can include lung tissue, gas, skeletal tissue and muscle tissue. However, it is particularly preferred that the tissue is porous which comprises a composite structure made up of tissue and gas or has regions of high and low density such as that found in bone tissue.

Preferably the tissue is of the respiratory system. More preferably the tissue is lung tissue or from the upper airway of the respiratory system. Preferably the upper airway includes the buccal region extending to the trachea before entering the lungs.

Throughout the description and claims of this specification, the word "comprise" and variations of the word, such as "comprising" and "comprises", is not intended to exclude other additives, components, integers or steps.

An understanding of various theoretical aspects of sound transmission in tissue is useful for the use of bio-acoustic data.

A unique feature of sound propagation through the lung parenchyma is that the sound velocity is less than that expected for either tissue (1500 ms$^{-1}$) or air (343 ms$^{-1}$). This can be explained, in part, by examining the basic relationship between sound velocity v and the physical properties of the lung tissue through which the sound is propagating. This relationship is:—

$$v = \frac{1}{\sqrt{\rho C}} \tag{1}$$

where $\rho$ is the density and C is the volumetric compliance or inverse volumetric stiffness per unit volume. In determining the velocity of sound in air, substituting an air density of 1.2 kgm$^{-3}$ and an air compliance of 7.14×10$^{-6}$ Pa$^{-1}$ yields a sound velocity in air of 342 ms$^{-1}$.

Rice (1983) has shown that this relationship also holds for composite porous materials with a closed cell structure which is similar to that of the lung, but where $\rho$ and C are replaced by the tissue's average or composite values. Expressing these values in terms of the volumetric fraction of tissue h and of gas (1–h) and the constituent densities and compliances gives tissue density:

$$\rho = (1-h)\rho_g + h\rho_t \tag{2}$$

and volumetric compliance:

$$C = (1-h)C_g + hC_t \tag{3}$$

where $\rho$, $\rho_g$, $\rho_t$ are the composite, gas and tissue densities respectively and C, $C_g$, $C_t$ are the composite, gas and tissue volumetric compliances respectively.

Substituting equations (2) and (3) into equation (1) yields an expression which relates sound velocity through a composite structure to the volumetric fraction and the physical properties of both the tissue and gas which compose the material:

$$v = \frac{1}{\sqrt{((1-h)\rho_g + h\rho_t)((1-h)C_g + hC_t)}} \tag{4}$$

It must also be noted that the density of air is approximately 3 orders of magnitude less than that of most tissues and the volumetric compliance of air is some 4 orders of magnitude larger than that of most tissues. This can be used to determine the velocity of sound propagation through the lung for a range of volumetric fractions which are likely to be seen in the lung, (0.05 at TLC to 0.5 to 0.9 for a fully atelectatic/collapsed lung). These velocities can be determined by simplifying equation 4 as follows:

$$v = \frac{1}{\sqrt{h(1-h)}} \frac{1}{\sqrt{\rho_t C_g}} \tag{5}$$

Figure 3:
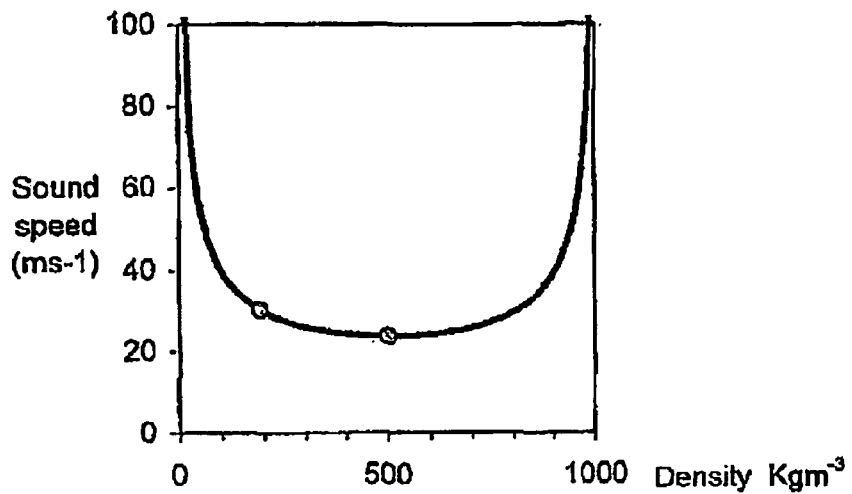
FIG. 3 illustrates the relationship between sound velocity and the volumetric fraction of tissue h and the average lung density.

Equation 5, in combination with FIG. 3 illustrates the dependence that sound velocity has on the volumetric fraction of tissue, the volumetric fraction of air, the tissue density and the gas compliance. The tissue compliance and the gas density play essentially no role in the determination of velocity.

Sound velocity in composite materials is determined in part by the product of the tissue density and the gas compliance. The result of this is that the lung parenchyma appears to act like homogeneous mass-loaded air as far as sound propagation is concerned, such that the velocity of sound propagation through the tissue is markedly slower than through air. Substitution of known values for tissue density, $\rho_t$ and gas compliance, $C_g$ in equation 5 gives:

$$v = \frac{11.82}{\sqrt{h(1-h)}} \tag{6}$$

Differentiation of v in equation 6 with respect to h determines a minimum value for velocity at h=0.5 where v=23.6 ms$^{-1}$. For values of h<0.5 the velocity increases with decreasing lung density and conversely for h>0.5 the velocity decreases with decreasing lung density. This is clarified by way of illustration in FIG. 3.

The quadratic properties of equation 6 result in the presence of two values for h for any particular value of measured velocity. These values are:

$$h = 0.5 \pm \sqrt{0.25 - 139.56/v^2} \tag{7}$$

Therefore, the determination as to whether h is above or below 0.5 must be made on physical grounds or by making paired velocity measurements where h is changed between measurements. The direction of the associated change in velocity (increasing or decreasing) can then be used to indicate whether h is above or below 0.5. Therefore, the volumetric fraction of tissue and gas in the lung and hence lung density can be determined directly from measuring the velocity of sound as it propagates through the tissue.

The sound may be introduced in any non-invasive manner, such as by percussion, or using any mechanical, electrical or other transducer which is capable of generating acoustic sounds. It is preferable that the sound which is introduced to the tissue possesses properties which allow it to easily be distinguished from environmental noise which may be present. Examples may include a single tone or a sinusoidal wave. In a preferred embodiment of the invention, a pseudo-random noise is produced by an electro-acoustic transducer and introduced into the tissue. The transducer is preferably attached to the surface of the biological tissue through which sound velocities are being measured. It is preferred that the pseudo-random noise signal which is used has characteristics which are similar to a white noise signal, but with mathematical properties which allow its amplitude to be defined at any moment in time. Furthermore, it is preferred that introduction of the pseudo-random noise signal to the tissue occurs in bursts, preferably of 0.1 to 20 seconds duration, and the sounds are produced preferably with frequencies which range from 20 Hz to 25 kHz and at a sound pressure level of between 1 and 100 Pascal.

The sound can then be recorded at a location spaced from the position at which the sound is introduced, preferably on the surface of the biological tissue which is spatially distinct from the location of the transducer, using a sound detection means such as a microphone or a vibration detector, such as an accelerometer, which has a frequency response that is flat in the acoustic region, preferably between 20 Hz and 25 kHz. It is preferred that there are at least two of these detectors used to measure the sound, wherein one detector is positioned near a sound-generating acoustic transducer, and another is located at a position spaced from the first position of the tissue being assessed. This enables the sound pressure level, phase, and frequency content of the signal which is produced by the acoustic transducer (the input signal) to be accurately defined before it is detected by the spatially separated second detector. Placement of the second detector is preferably substantially in line with the acoustic transducer and the first detector.

The detector or preferably a microphone output may be amplified using low noise isolation amplifiers and band-pass filtered with cut-off frequencies and roll-off characteristics which depend on the acoustic properties of the tissue which is being assessed. For example, for measurements made on the neonatal lung, the pass band is preferably between 50 Hz and 5 KHz with a roll-off which corresponds to that of a $4^{th}$ order linear phase filter. These filters remove any very low frequency environmental noise (e.g. below 10 Hz) that can adversely affect the performance of auto-scaling amplifiers into which the filtered signal may be fed.

The amplified output signal from the detector or microphone can then be processed by any means necessary, and a cross-correlation analysis of the input and output signals performed.

The cross-correlation function can be calculated using the output of the microphone which is located in close proximity to the acoustic transducer as the input signal, x(t) and the output of the second microphone located on the other side of the tissue as the output signal, y(t) wherein the cross-correlation function can be calculated as $$R_{xy}(\tau) = \lim_{T \to \infty} \frac{1}{T} \int_0^T x(t) y(t + \tau) dt$$

where T is the observation time, and $\tau$ is the delay time between x(t) and y(t) at which $R_{xy}(\tau)$ is calculated.

The impulse response of the system in the time domain can also be determined. It is preferable that the impulse response then undergoes Fast Fourier Transformation so that the signal is transformed into the frequency domain and the transfer function of the tissue can be determined. This transfer function provides a quantitative indication of the characteristics of the tissue, wherein:
(a) the magnitude of the transform provides data relating to the transmission of the sound as it propagates through the tissue as a function of frequency (Rife and Vanderkooy, 1989); and
(b) the phase of the transform (after "unwrapping") can be used to calculate the phase difference, time delay and velocity of the sound for each frequency that is present in the pseudo-random noise signal which is introduced to the tissue by the acoustic transducer.

Commercially available acoustic hardware and software packages may be used to generate the pseudo-random noise signal, and to perform initial data processing. External noise which is not introduced to the tissue as part of the pseudo-random noise signal is strongly suppressed by the cross-correlation process thereby improving the quality of the measurements made.

A separate analysis of the relative transmission of the sound through the tissue can be used to identify resonant and anti-resonant frequencies of the tissue which is being assessed. Changes in these frequencies can then be used to assess regional differences in tissue topology which may be related to pathology.

Despite numerous experimental investigations (Kraman 1983, Goncharoff et al. 1989, Wodicka and Shannon 1990) of trans-pulmonary sound transmission where the source of sound is placed at the mouth, there has been no theoretical model which described sound transmission through the thorax. The present invention uses a simple model, based on the double wall transmission model that is used in architectural acoustics (Fahy 1985) to describe the sound attenuating effect of double walls separated by a compliant air layer, as is present in the lung.

Figure 4A:
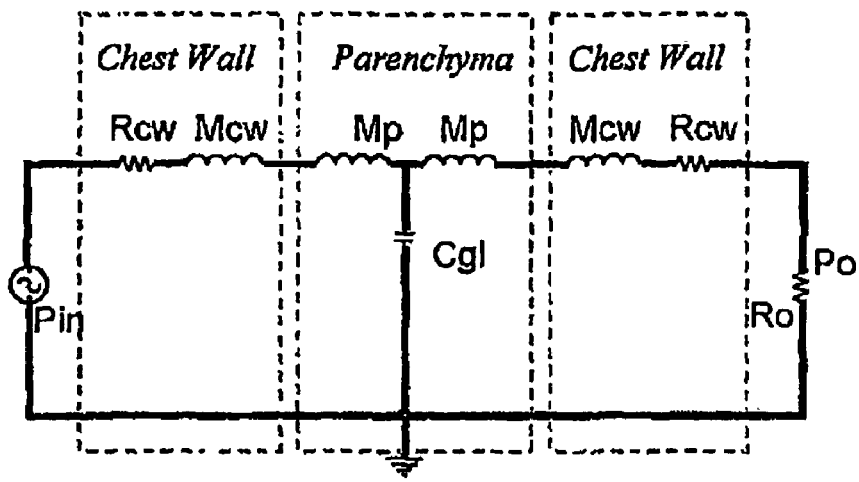
FIG. 4(a) illustrates an electric circuit which models the acoustic characteristics of the thorax.

The essential features of this model as it relates to the thorax can be represented by an electrical equivalent circuit that can be used to describe the pertinent features of sound transmission through the thorax. This model is illustrated in FIG. 4(a). This approach to the analysis of acoustic transmission across the thorax facilitates analysis using sophisticated circuit emulation software such as SPICE to explore the effect of changing model parameters. In the equivalent electric circuit model where:

$R_{cw}$ is the loss component associated with the chest wall and parenchyma;

$M_{cw}$, $M_p$ is the surface mass of the chest wall and parenchyma respectively;

$C_{gl}$ is the lung gas compliance;

$P_{in}$, $P_o$ are the acoustic input and output sound pressure levels respectively; and $R_o$ is the acoustic impedance of free space (414 MKS Rayls).

Figure 4B:
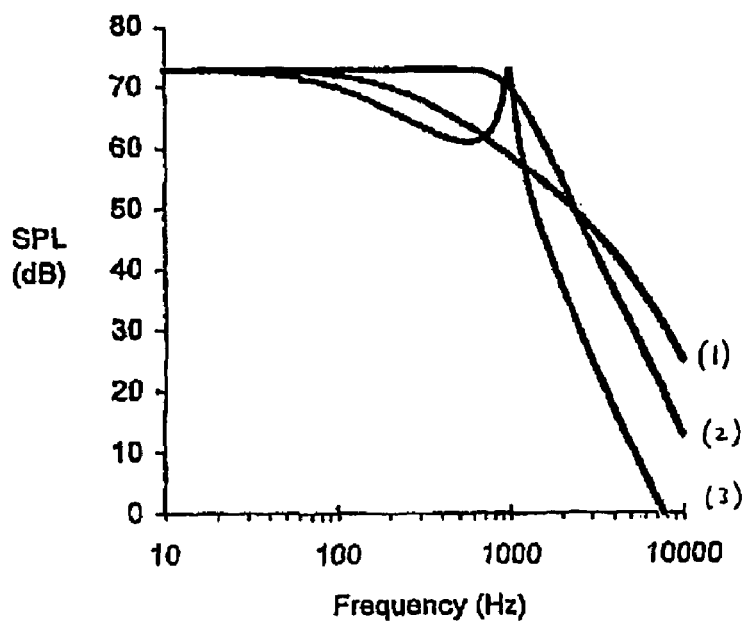
FIG. 4(b) illustrates (1) large, (2) moderate and (3) small acoustic losses as measured using the electric circuit model and which represents the output SPL as would be measured at a chest microphone when the input SPL is 105 dB.

As illustrated in FIG. 4(b), the model can be used to simulate the effect that changing $R_{cw}$ has on the transfer function of the equivalent circuit which represents the chest. This transfer function can be described mathematically as $P_o(f)/P_{in}(f)$ where f is the frequency and $P_{in}(f)$ and $P_o(f)$ are the input (transducer) and output (chest microphone) sound pressure levels (SPL) respectively. As $R_{cw}$ is decreased, the transfer function becomes progressively more peaked or resonant as illustrated by curves 1 to 3 in FIG. 4(b).

At sufficiently high frequencies, the output sound pressure level for all three curves falls asymptotically at a rate of 60 dB per decade. As the frequency is increased above the resonant frequency, the response is dominated by the inertial mass of the proximal and distal chest walls, and the shunt gas compliance of the lung. These act together to produce the 60 dB per decade fall-off, such that the thorax is, in effect, acting like a third order low-pass electrical filter. Analysis of the equivalent circuit, neglecting losses, shows that the resonant frequency of the thorax, $f_o$, can be determined using:

$$f_0 = \frac{1}{2\pi} \sqrt{\frac{2}{C_{gl}(M_{cw} + M_p)}} \tag{8}$$

Figure 5A:
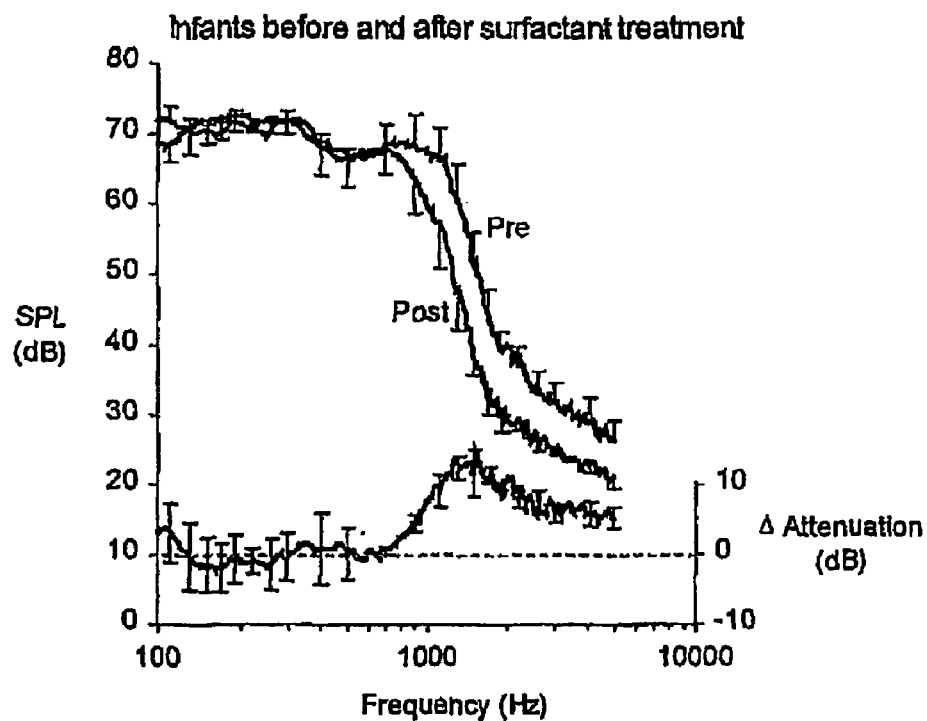
FIG. 5(a) shows the SPL measured at a chest microphone, recorded before (pre) and after (post) administration of surfactant in 3 preterm infants, wherein the sound level produced by the transducer was 105 dB (Sheridan 2000).
Figure 5B:
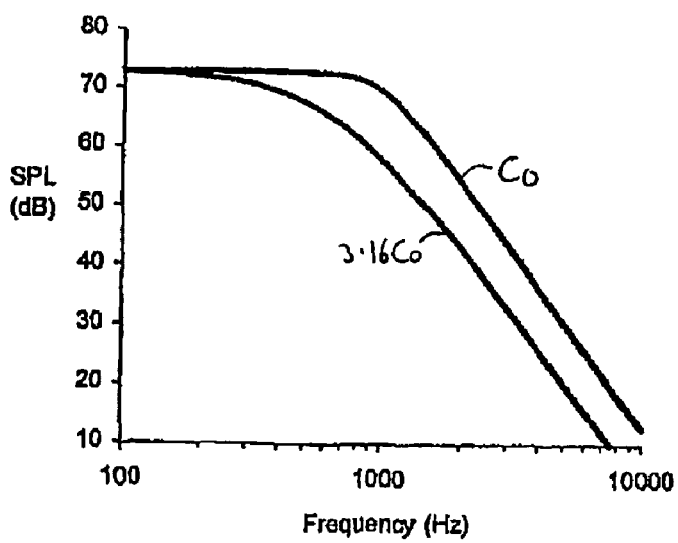
FIG. 5(b) shows the electric model simulation of FIG. 5(a), demonstrating the change in the SPL measured at the chest wall following a 3-fold increase in lung gas compliance, wherein the sound level produced by the transducer was, again, 105 dB.

Furthermore, if the transfer function is measured at $f_o$ and at another frequency well above $f_o$, say, $3f_o$ then using an analysis of the equivalent circuit, an explicit expression for lung gas compliance, $c_{gl}$, can be deduced in the form $$C_{gl} = \frac{4.18 \times 10^{-2} G}{f_0} \quad (9)$$

where $G=|P_o(f)/P_{in}(f)|$ and is the magnitude of the transfer function of the thorax measured at $3f_o$. This equation has been verified using SPICE simulation. It follows that gas volume $V_{gl}$ can be computed using equation 9:

$$V_{gl} = \gamma P_o C_{gl} \quad (10)$$

where $\gamma$ is the adiabatic gas constant and $P_o$ is the atmospheric pressure A further important application of this model is illustrated in FIGS. 5(a) and 5(b). FIG. 5(a) shows the experimentally measured thorax transfer function in a preterm infant soon after delivery but before surfactant administration (pre) and after the administration of surfactant (post) (Sheridan 2000). There is a steep fall-off in sound transmission for frequencies above 1000 Hz pre-surfactant and the leftward shift of this fall-off accompanied by an increase in attenuation of 10 dB following surfactant administration. A similar 10 dB change can be simulated in the model by increasing $C_{gl}$ by about a factor of three while maintaining other parameters constant as illustrated in FIG. 5(b). Although a measurement of lung gas compliance was not made during these experiments, and is not feasible using currently available technology, it would be expected that such an increase in compliance (associated with an increase in gas volume) would occur after surfactant administration.

An important component of acoustic transmission which can be modelled using the equivalent electric circuit is the loss component Rcw illustrated in FIG. 4(a) which includes acoustic loss in the chest wall and parenchyma. Because the chest wall is acoustically thin, the dissipative loss in the wall is negligible but the loss in the parenchyma, which includes a large number of serial mass-compliance interfaces formed from the tissue and gas comprising the parenchymal structure, may be considerable. One model that has been proposed to account for acoustic loss in the parenchyma comprises air bubbles in water, for which an analysis already exists. In this model, absorption occurs because acoustic work is required to alternately compress and expand these bubbles.

It has been shown (Wodicka 1989) that the plane wave attenuation produced by N bubbles over distance x is given by:

$$P(x) = P_0 e^{-\left(\frac{N\sigma}{2}\right)x} \quad (11)$$

where $\sigma = 16\pi^2 r_o^4 \rho_t c_t R/\{R^2+(\omega M-1/\omega C)^2\}$

P(x) is the SPL at x
$P_o$ is the SPL at x=0
$r_o$ bubble radius
$c_t$ sound speed in tissue
R,M,C are the effective mechanical resistance, mass and compliance of the bubbles respectively Attenuation, $$\alpha = \frac{P(x)}{P_0}$$

in dB/cm can then be written as:

$$\alpha = 4.35 N\sigma \quad (12)$$

This is a complex function of R,M,C but a simplified expression for the attenuation can be deduced by recognising that the acoustic vibration of the bubbles (alveoli) is dominated by bubble compliance c at frequencies which are much lower than resonance (ie. $<\approx 10$ kHz for realistic alveoli sizes). Therefore, attenuation can be reduced to:

$$\alpha = 2.36 \times 10^{-2} r_o^6 f^3 N \quad (13)$$

The number of bubbles per unit volume N is approximately related to the gas fraction (1–h) by:

$$N = \frac{3(1-h)}{4\pi r_0^3} \quad (14)$$

hence equation 13 can be written as $$a = 1.35 \times 10^{-3} \frac{f^3(1-h)^2}{N} \quad (15)$$

Figure 6:
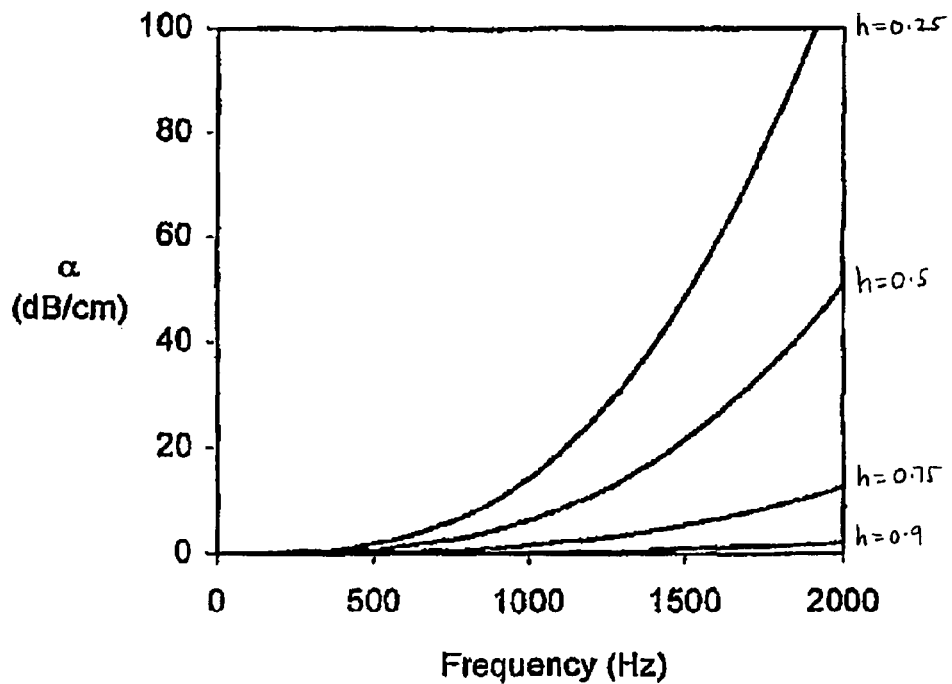
FIG. 6 shows the relationship between frequency and the calculated attenuation coefficient α plotted with tissue fraction h as a parameter.

From these equations, it can be seen that:
(a) absorption is related to the square of the gas fraction (1–h); a small increase in the tissue fraction h is associated with a marked decrease in high frequency attenuation (FIG. 6). This may explain the increased transmission of sound across the chest wall which can be observed clinically at high frequencies, following pneumonic consolidation of the lung; and
(b) attenuation is a strong function of both the frequency f and the alveolar radius $r_o$. This may explain, in part, the rapid fall-off in transmitted sound at high frequencies seen in both adult and neonatal subjects. The dependence on bubble radius may explain the reduced transmission through the thorax during emphysema.

Furthermore, these equations indicate that:
(a) absorption is related to the square of the gas fraction (1–h); and
(b) Sound transmission attenuation is s strong function of both the frequency and the alveolar radius.

Using these relationships between sound transmission velocity in tissues and the tissue characteristics themselves, it is possible to obtain a workable relationship between acoustic measurements and lung pathology or the pathology or condition of other biological tissues.

This method provides a virtually continuous real-time measurement of tissue characteristics by analysing the velocity and attenuation of a defined sound as it propagates through the tissue. The method is applicable in both adults and infants, and for humans and animals. In particular, the present invention can be used in the determination of respiratory conditions in infants who cannot co-operate with presently available conventional stethoscopic methods of respiratory condition analysis which requires vocal co-operation. It is also useful where the patient is critically ill, is unconscious, or is unable to respond or generate a sound which can be used to determine lung condition.

In a preferred aspect of the present invention, there is provided a method of determining a state of the upper airways in a respiratory tract in a patient in situ, the method including introducing a sound at first position in the upper airways and detecting the sound after it has travelled through the upper airways.

The state of the upper airways may include any condition of the upper airways such as obstructed or open airways. Measurement of the closure or collapse of the upper airway is particularly useful for conditions such as in obstructive sleep apnea or OSA.

Apnea, and particularly Obstructive Sleep Apnea (OSA) is associated with closure of the upper airway and lapses in respiration during sleep. Using the present invention, a pseudo-random noise may be introduced into the airway using an acoustic transducer which conducts the sound from a location in the upper airway preferably via a Silastic nosepiece adapter. During normal respiration, the airway is open and the sound is transmitted via the airway to the lung via the trachea, where it subsequently propagates through the lung parenchyma and thorax to the surface of the chest. A sound-detection device such as a microphone may be attached in the chest region. Variations in the sound level which is measured at the chest region can then be used to model the degree of upper airway patency. The chest region may include the region extending from below the buccal cavity to below the lung.

Preferably, the microphone is placed on the upper chest region generally below the neck and just above the lung.

When the airway is closed, the transmission of sound through the tissue decreases so that it may be undetectable by a microphone located on the chest. Therefore, when the sound falls below a certain value, it is likely to indicate the closure of the airway. When the signal which is detected by a microphone detector or located on the chest region falls below a certain preset limit, an alarm is activated indicating obstruction of the airway. This alarm may wake up the subject, which will most often result in the subsequent reopening of the airway, or it may alert attending staff to a patient who is being monitored for OSA or any other airway dysfunction. There are several benefits associated with this method for detecting airway obstruction or closure which include:

(a) the technique is non-invasive;
(b) the technique can be used in new-borns and adults alike, and in humans or in animals;
(c) the technique monitors patency of the airway, not depletion of oxygen or lack of movement as is the case in other apnea detection devices. As a result of this, the susceptibility of the subject to oxygen depletion is detected before depletion itself occurs, thereby allowing for suitable and timely intervention and reducing the likelihood of discomfort and tissue damage which can be caused by extended lapses or pauses in regular respiration and oxygen deprivation. This method can for example be used to set the optimal level of CPAP to apply to a patient in order to maintain airway patency.

In yet another preferred aspect of the present invention, there is provided a method of monitoring lung condition in situ said method comprising:

introducing a sound transthoracically so that the sound travels from one side of the thorax, through the lung, to another side of the thorax;

measuring the velocity and attenuation of the sound as it travels from one side of the thorax, through and across the lung, to the other side of the thorax; and correlating the attenuation and sound velocity and velocity dispersion to lung condition.

Previous work shows that measurement of sound velocity alone may provide a technique for assessing lung density and gives an insight into the degree of lung inflation. However, no attempt has been made to evaluate the potential utility of sound velocity and attenuation as a clinical tool.

Lung condition may be selected from the group including but is not limited to:

(a) lung tissue density;
(b) lung gas volume;
(c) regional collapse (atelectasis);
(d) regional blood volume, interstitial oedema; and
(e) focal lung pathology such as tumour and global lung disease such as emphysema.

These lung conditions may then be compared with the condition of a normal, healthy lung.

To measure lung condition, the method of the present invention is preferably applied by introducing a sound to the thorax and hence to the lung preferably by applying an acoustic transducer to the thorax on one side of the chest and calculating the sound velocity and attenuation using a detector or microphone which is attached to the other side of the chest and which detects the transmitted sound. Previous measurements of lung condition or volume have been made by introducing sound to the lung tissue via the trachea. However, there are problems associated with this method for the lung which result from the unknown distance between the trachea and chest wall, and an inability to selectively distinguish the effects of the airway from the effects of the lung parenchyma on the velocity of the introduced sound. In other measurement techniques, the sound is generated by the subject by respiration, coughing or speech, or is introduced through percussion. However, this presents a key limitation because the acoustic properties of these sounds are subject-dependent and beyond control, particularly in the newborn infant, who is unable to reliably produce the desired sound on command.

The present invention exhibits a novel approach to examining the acoustic properties of the biological tissues, including the upper airways and of the thorax, by introducing sounds with a known and precisely defined spectral content as the investigative tool. For the lung, by utilising this sound which is introduced directly to the wall of the thorax, and by recording the sound after it is transmitted across the thorax, uncertainties associated with noise introduced via the trachea are eliminated. Without being restricted by the theory, research suggests that the lung tissue type which is primarily responsible for changes in sound velocity as it propagates through the thorax is the lung parenchyma; the contribution to changes in sound wave velocity and attenuation which is made by the airways is insignificant.

Many lung diseases are associated with characteristic features that can be detected using auscultation of the chest (Lowe and Robinson, 1970). In the normal lung, frequencies above 300-400 Hz are heavily attenuated by thoracic tissue, and on auscultation, respiration sounds are soft, conversational sounds are muffled, and whispered sounds are inaudible. By contrast, pneumonic consolidation greatly reduces the attenuation of high frequency sounds, resulting in characteristic respiration sounds known as 'bronchial breathing' and strong transmission of whispered (high-frequency) sounds known as 'whispering pectriloquy'. A pleural effusion on the other hand, classically gives rise to increased attenuation of low frequency sound, causing vocal sounds to have a high pitched nasal quality known as 'aegophony'.

Studies have been published which examine the effect of lung condition on sound attenuation in the healthy human lung. However, these studies have failed to measure the effect of lung inflation on sound attenuation. The present invention utilises transthoracically introduced sound and preferably measures the sound velocity and sound attenuation to determine lung condition. Lung conditions assessed using the present invention may include lung density and lung volume. However, other lung conditions may be determined by correlating changes in sound velocity and sound attenuation which are associated with known lung conditions with sound velocities and attenuation which are measured using a normal, healthy lung.

Tissue density may be measured using sound velocity alone. However, sound attenuation may also be introduced as a parameter for the determination of tissue density. Tissue density may be a measure of the amount of fluid or blood in the tissue. In the lung, it may also indicate gas volume, regional collapse (atelectasis), regional blood volume, interstitial oedema and both focal lung disease (eg tumour) and global lung disease (eg emphysema) which may be compared with a normal, healthy lung.

In yet another preferred aspect of the present invention there is provided a method of measuring lung inflation, said method including:
  introducing a sound transthoracically so that the sound travels from one side of the thorax, through the lung, to another side of the thorax;
  measuring the velocity and attenuation of the sound as it travels from one side of the thorax, through and across the lung, to the other side of the thorax; and
  correlating changes in sound velocity and attenuation with lung volume and inflation.

Lung gas volume is inversely proportional to lung density and may be measured using sound velocity and preferably sound attenuation. Furthermore, measurement of the velocity of a sound as it propagates from one side of the thorax through the lung tissue to the other side of the thorax can be correlated with a change in lung volume (inflation). This may be done in isolation, or during or after clinical interventions which alter the degree of lung inflation. Measurements taken may include:
a) before and at intervals after treatment with surfactant;
b) before and at intervals after commencement of Continuous Positive Airway Pressure (CPAP) to recruit lung volume in the presence of hyaline membrane disease and/or atelectasis;
c) before and at intervals after the commencement of mechanical ventilation; and
d) before and immediately after endotracheal tube suctioning.

The degree of change in the sound velocity and preferably also of sound attenuation may be used together to provide a more conclusive indication of the degree to which the lung is inflated. Lung inflation may be determined using a single measurement, or it may be determined continuously, thereby enabling the monitoring of progress of lung disease and its treatment. This has particular value in the treatment and monitoring of lung disorders in premature babies over a period of time.

In yet another preferred aspect of the present invention, there is provided a method of predicting chronic lung disease in infants said method including:
  introducing a sound transthoracically so that the sound travels from one side of the thorax, through the lung, to another side of the thorax;
  measuring the velocity and attenuation of the sound as it travels from one side of the thorax, through and across the lung, to the other side of the thorax; and
  comparing the measured sound velocity and attenuation with that of a normal lung in the absence of chronic lung disease.

Abnormal lung density due to over- or under-inflation of the lung may be associated with increased lung injury and the propensity for development of chronic lung disease in infants. Therefore, measurements of sound velocity and attenuation (which relate to lung density) in a premature infant may allow inflation to be optimised and risk of chronic lung disease to be reduced.

Measurements of the sound velocity and sound attenuation may be made on days 1, 2, 3, 5, 7, 10 and 14 or any interval thereof and then at weekly intervals until about 36 weeks. As a comparison, and to complement measurements made using the present invention, absolute lung volume may be measured using the gold-standard and long-established helium dilution technique at the time of the acoustic measurements. Results taken from infants who subsequently develop chronic lung disease (defined either as oxygen dependency at 28 days or at a postmenstrual age of 36 weeks) may be compared with results from those who do not.

In yet another preferred aspect of the invention there is provided a method of diagnosing lung disease, said method including measuring lung density including:
  introducing a sound transthoracically so that the sound travels from one side of the thorax, through the lung, to another side of the thorax;
  measuring the velocity and attenuation of the sound as it travels from one side of the thorax, through and across the lung, to the other side of the thorax; and
  correlating sound velocity and attenuation with lung density and comparing the density of the lung being diagnosed with the density of a normal lung to determine if the lung being diagnosed is diseased.

A similar technique can be used to assist in diagnosing lung disease wherein again, a sound is introduced to the thorax such that it travels from one side of the thorax, through the lung, to another side of the thorax. The sound velocity and preferably attenuation which is measured is then compared with that of a normal, healthy lung. Since lung disease often manifests in reduced lung volume, a comparison can be used, again, to provide an indication as to whether a subject's lung exhibits lung disease. Common lung diseases may include emphysema, asthma, regional collapse (atelectasis), interstitial oedema and both focal lung disease (e.g. tumour) and global lung disease (e.g. emphysema). Each of these may be detectable when measurements of the velocity and attenuation of a sound which is transmitted through a diseased lung are compared with those from of a lung in normal condition.

In yet another preferred aspect of the present invention, there is provided a method of preventing lung injury, said method including monitoring lung condition by:
  introducing a sound transthoracically so that the sound travels from one side of the thorax, through the lung, to another side of the thorax;
  measuring the velocity and attenuation of the sound as it travels from one side of the thorax, through and across the lung, to the other side of the thorax;
  correlating the sound velocity and attenuation with lung volume; and
  maintaining a lung volume at an optimal volume such that the lung is substantially free of atelectasis or over-inflation (volutrauma).

The present invention provides a reliable method for monitoring lung density and volume in situ. However, it can also be used to provide a method of preventing lung injury by again, introducing a sound transthoracically so that the sound travels from one side of the thorax through the lung to another side of the thorax. The velocity of the sound can be measured as it travels from one side of the thorax through the lung to the other side of the thorax, and the measurement can be used to indicate the volume of the lung which can then be used in the maintenance of an optimal lung volume which is substantially free of atelectasis or over-inflation (volutrauma). These optimal lung volumes are illustrated graphically in FIG. 1, wherein there exists a window inside which the possibility of causing lung injury can be minimised. This window is framed by under-inflation and over-inflation lung volumes. If lung volume is maintained inside this window, the likelihood of lung injury will be reduced. However, to ensure the volume does not rise excessively and does not drop to the level of atelectasis, it is necessary to constantly monitor the lung's volume.

In another aspect of the present invention there is provided an apparatus for determining characteristics of biological tissues, the apparatus including:
  a sound generating device which generates a sound;
  a recording device which records the sound after it has travelled from one position of the biological tissue, through the tissue and to another position of the tissue;
  an analysis device which calculates the velocity and attenuation with which the sound travels through the tissue, and which can preferably perform spectral analysis on the data recorded.

In yet another preferred aspect of the present invention, there is provided an apparatus for monitoring lung condition, said apparatus including:
  a sound generating means to generate a sound transthoracically so that the sound travels from one side of the thorax, through the lung, to another side of the thorax;
  a recording means to record the sound after it has travelled from one side of the thorax, through and across the lung, to the other side of the thorax;
  an analysis device which calculates the attenuation and velocity with which the sound travels from one side of the thorax, through and across the lung, to the other side of the thorax, and which can preferably perform spectral analysis on the data recorded.

The present invention can be used to provide a monitoring system which measures sound velocity and preferably combines sound velocity data with measurements of sound attenuation in order to determine the level of lung inflation in a subject. Spectral analysis of the impulse response can indicate frequency components in the sound signal which are more prominent than others and which may be an indicator of pathological or abnormal tissue. Preferably the lung condition is monitored by an independent measure of lung density or lung volume.

The benefits associated with the application and detection of acoustic signals to biological tissues is not limited to the lungs, airways and other tissues associated with respiration. The present invention can be used to detect densities of other porous structures and composite biological tissues which have high or low densities, wherein the ratio of solid to porous tissue gives rise to the change in velocity and sound attenuation which is measured.

The present invention will be more fully described with reference to the accompanying examples and figures. It is to be understood that the description following is illustrative only and should not be taken to be limiting in any way, or as a restriction on the generality of applications for the invention previously described.

EXAMPLES

Example 1

Measurement of Lung Volume in Adults

Figure 2:
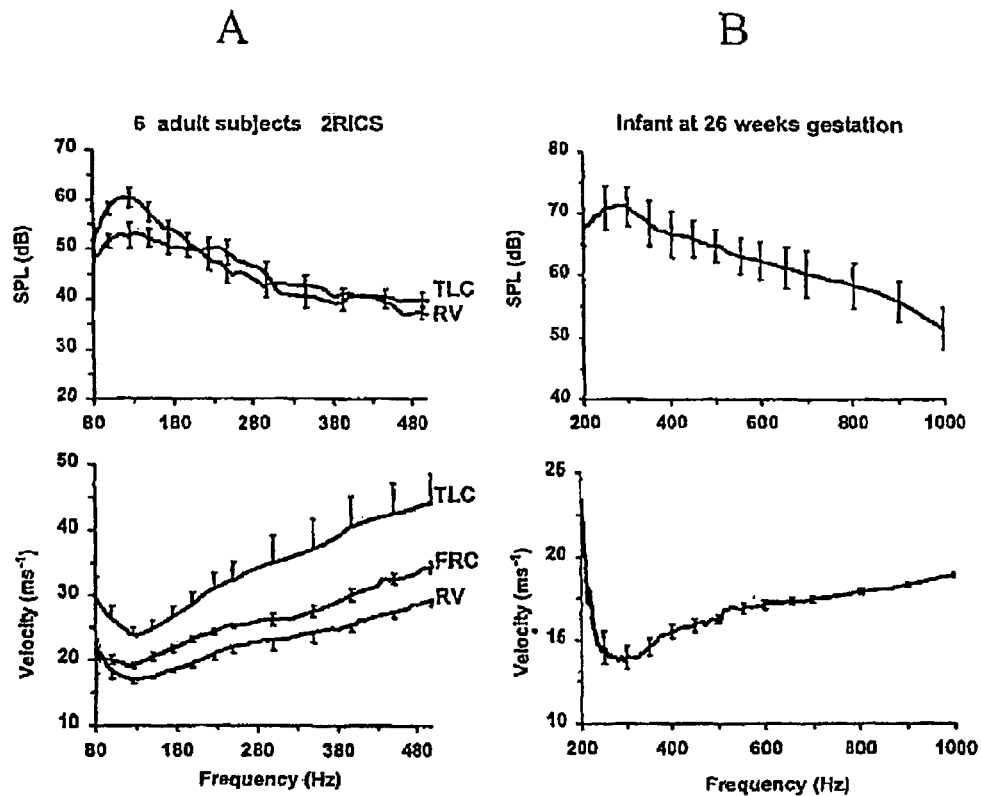
FIG. 2 shows (A) Sound pressure level (dB) and sound velocity (m/s) versus frequency (Hz) for pooled results taken from 5 adult subjects during breath-holds at residual volume (RV), functional residual capacity (FRC) and total lung capacity (TLC). (B) shows results from an infant of 26 weeks gestation with healthy lungs, each data point representing the pooled mean ±S.E. of 5 measurements. The results were obtained from a reference position in the adult with the transducer at the $2^{nd}$ right intercostal space on the anterior chest wall and in the newborn over the right upper chest. In both adult and infant, the microphone was placed on the opposite wall of the chest directly in line with the transducer.

In 5 healthy adult subjects, the velocity and attenuation of sound which was transmitted from one side of the chest to another, in a range of frequencies from 50-1000 Hz was measured at a number of defined positions on the chest. These measurements were taken while the lung volume was varied between Residual Volume (RV) and Total Lung Capacity (TLC). A reference position was established over the right upper zone of the chest. Using this position, a region in the frequency spectrum (around 100-125 Hz) where sound attenuation was much reduced and where the degree of attenuation was directly related to lung inflation (see FIG. 2A, upper panel) was found. The difference in attenuation between RV and TLC was approximately 7.5 dB and statistically significant ($P=0.028$). Further, it was found that sound velocity was low, averaging around 30 m/sec, and it showed a clear and strong sensitivity to the degree of lung inflation, being appreciably faster at TLC than at RV (FIG. 2A, lower panel). In this study evidence was found which indicated that the effect of inflation on velocity and attenuation varies at different locations in the thorax, particularly in the lower zones. It is likely that this is, in part, attributable to the location of the heart and liver (at RV) in the sound path.

The method of analysis permits determination of phase shift, and therefore velocity as a function of frequency. This work has shown that the speed of sound in the lung parenchyma is dispersive, or frequency dependent, over the range of frequencies studied. This is of considerable importance, since it is theorised that the relationship between velocity and frequency is dependent on regional compliance and inertial (ie mass dependent) properties of the lung. These properties may provide valuable information about the lung since they are partly determined by the condition of the alveolar septum, the degree of fluid infiltration of the lung parenchyma, and the extent of atelectasis.

Preliminary pilot data were collected from newborn infants in the neonatal intensive care unit. FIG. 2B represents a sample result from an infant of 26 wks gestation with healthy lungs, illustrating that measurements can be made using the present invention with a subject who cannot co-operate and who must be studied in the noisy intensive care setting. Interestingly, the frequency region over which sound attenuation is least in the newborn is higher (approximately 300 Hz) than in the adult. In addition, although the relationship between velocity and frequency has a nadir at about 300 Hz compared with 125 Hz in the adult, the dispersive nature of sound velocity which is evident in the adult is also present in the infant.

Example 2

Measurement of Lung Density in Rabbits

Experiments were conducted in 1-2 kg New Zealand white rabbits. These animals were chosen for their similarity in size to the human newborn and their widespread use as a model of neonatal surfactant deficiency. Animals were anaesthetised with intravenous thiopentone, before performing a tracheostomy during which a 3 mm endotracheal tube was inserted into the airway to allow ventilation using a conventional neonatal ventilator (Bournes BP200). Maintenance anaesthesia was achieved with intravenous fentanyl. The chest was shaved and a microphone and transducer secured in various pre-defined positions, including a reference position over the right upper chest. The animal was then placed in a whole body plethysmograph to monitor absolute lung gas volume at intervals throughout the experiment. Tidal volume was monitored continuously with a pneumotachograph attached to the tracheostomy tube. The sound velocity and attenuation was determined at each location of the where a microphone was situated, and each observation was the average of 10 repeated measures.

The effect of changes in lung density as a result of lung disease on sound velocity and attenuation was examined by comparing results from 3 groups of rabbits with differing lung conditions:

Group 1—Normal lungs (n=10)
Group 2—Lungs rendered surfactant deficient by saline lavage (n=10)
Group 3—Lungs rendered oedematous by inflation of a left atrial balloon catheter (n=10).

Within each group of animals the effect of changes in lung density, resulting from changes in degree of lung inflation, was examined by making measurements under dynamic and static conditions.

(1) Dynamic measurements during mechanical ventilation. Sound velocity and attenuation may be measured during mechanical ventilation at various levels of positive end-expiratory pressure (PEEP) including 0, 5, 10, 15 and 20 $cmH_2O$. Absolute lung volume at end expiration, and tidal volume may be determined for each level of PEEP. A wide range of PEEP can be employed to ensure that observations are made over a wide range of lung volumes, from under-inflation to over-inflation and including optimal inflation.

(2) Static measurements during apnoea. Sound velocity and attenuation was measured while the lung was transiently held at constant volume after spontaneous respiratory effort had been suppressed by a brief period of hyperventilation. Various lung volumes from below functional residual capacity (FRC) to TLC were achieved by varying airway pressure between −10 and +30 $cmH_2O$. Studying the lung under static conditions allows observations to be made at the extremes of lung volume. These results were directly comparable to observations during breath-hold in adult subjects and enables verification of the cross-correlation technique used in the present invention which increases the system's robustness against interference from breath sounds.

(3) Static measurements post-mortem. At the completion of (2) above, a lethal dose of anaesthetic was administered and observations of sound velocity and attenuation were repeated across the same range of lung volumes as in (2). The trachea was then clamped at an inflation pressure of 10 $cmH_2O$ before dissecting the lungs so that they were free from the chest and so that their weight and density could be determined. In order to address the question of the regional differences in sound velocity and attenuation observed in the adult human study, final measurements were made of the acoustic properties of the excised lung at the same levels as those studied in the intact thorax. An important aspect of this analysis is that it allowed comparison of results obtained before and after death to establish whether the cross-correlation technique used is resistant to interference from cardiac sounds.

Example 3

Measurement of Lung Inflation in Infants

To be a valuable clinical tool, measurements of sound velocity and attenuation must be sensitive to changes in lung inflation that are of a clinically relevant magnitude. A test of whether measurable changes in sound velocity and attenuation which occurred after clinical interventions which were confidently predicted alter the degree of lung inflation was conducted. It was found that clinical interventions which cause a significant change in lung inflation are associated with changes in sound transmission and velocity which are measurable using the present invention.

Example 4

Prediction of Chronic Lung Disease

It is also necessary to determine whether evidence from acoustic measurements of abnormal lung density are indicative of either under-inflation or over-inflation, and associated with development of chronic lung disease as a result. It was found that abnormal lung density in the first few days of life was more common in infants who subsequently developed chronic lung disease than in those who did not. Serial measurements of sound velocity and attenuation in a population of pre-term infants (n=30) who, by virtue of their gestation (<30 weeks), are at high risk of developing chronic lung disease were made. In this population and using the present invention, it was estimated that about 65% of the population will still be oxygen dependent at 28 days of age, and about 30% will still be oxygen dependent at a postmenstrual age of 36 weeks.

Further aspects of the present invention as it relates to airways and to the determination of patency will now be described.

Figure 7:
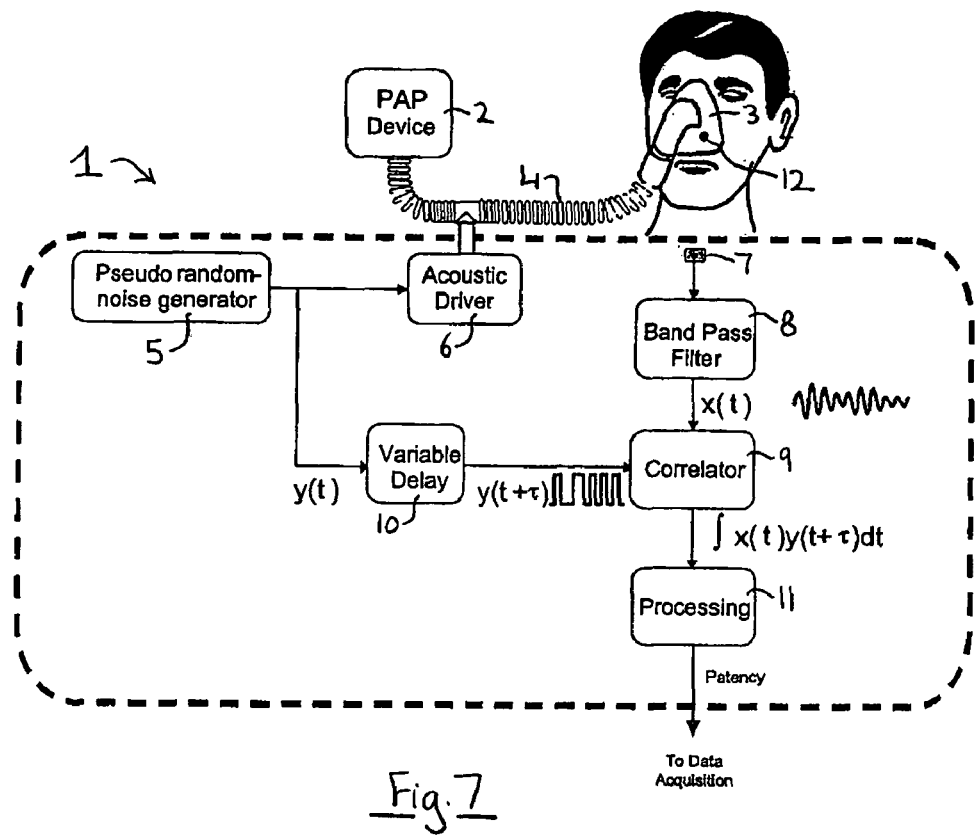
FIG. 7 is a schematic diagram of PAP apparatus utilising a patency detector according to one embodiment of the present invention.

Referring to FIG. 7, apparatus 1 for determining patency is shown attached to a respiratory assist device 2 that may be for example a positive airway pressure (PAP) device, e.g. a CPAP device or a variant thereof, such as a bi-level, intermittent or auto-titrating device. The PAP device 2 applies air under positive pressure to a patient nose mask 3 via a PAP line 4. The positive pressure helps to splint the airways of the patient open during sleep, and provides treatment for obstructive sleep apnea (OSA) in which the upper airways have a tendency to collapse or otherwise block during sleep.

The patency apparatus 1 is used to monitor airway patency. It can be used in the control of the PAP device 2, e.g. as an aid to determining when to apply positive pressure and to what degree.

The patency apparatus 1 includes an applied sound signal generator in the form of a pseudo-random noise generator 5 that provides a signal to an acoustic driver 6. The acoustic driver 6 injects a sound signal into the PAP line 4 based on the signal from the pseudo-random noise generator 5.

The sound signal applied to the PAP line 4 is made up of one or more frequencies in the audible frequency range, e.g. from 20 Hz to 20 KHz.

The use of an applied sound signal in the form of continuous white noise, or a tone or combination of tones masked with white noise, assists in patient comfort, as the applied sound is then not unduly disturbing to the patient. The signal may be for example Gaussian white noise, a pseudorandom noise such as MLS (maximum length sequence) noise or a noise sequence with a known structure. The signal could however in other embodiments be a tone or combination of tones. It could also be a pulsed signal.

The patency apparatus also includes a signal sensor 7 for detecting the sound signal generated by the acoustic driver 6 after it has passed through the PAP line 4, the mask 3 and the patient's upper airways, which may include e.g. the nasal cavity, pharynx, larynx and trachea, and could also include the buccal cavity, e.g. if sound is applied to the mouth rather than or in addition to the nose.

The sensor 7 may be placed in any suitable position, and in a preferred embodiment is placed in the region of the suprasternal notch. This area has been found to provide a satisfactory detected signal, with minimum attenuation of the applied signal, as the signal has to travel through less tissue than if it were placed at alternative locations on the body. The sensor may however be placed in other positions, and it has been found for example that with neonates satisfactory signals can be obtained with sensors placed on the anterior or posterior surfaces of the chest, or on the abdomen.

The acoustic driver 6 could be e.g. an electro-acoustic driver, and the neck sensor 7 could be e.g. a microphone, such as an electret microphone or an accelerometer. The output level of the acoustic driver 6 may be altered so as to find a balance between maximal injected signal strength and patient comfort.

The output of the sensor 7 (the detected sound signal) is passed via a band pass filter 8 to processing circuitry. The band pass filter 8 helps to reduce extraneous noise in the detected signal, so as to optimise the signal to noise ratio.

The patency of the patient's airway is determined based on variations in the detected sound signal. Thus, patency may be determined based on variations in the degree of attenuation of the applied sound signal after it has travelled through the patient's airways, e.g. through absorption, scattering, refraction and reflection of the signal.

Patency may for example be determined by comparing measured characteristics of the detected signal with reference characteristics and/or by comparing different portions of the detected signal with one another.

In the present embodiment, the signal transmitted through the airway x(t) is cross-correlated in a correlator 9 with a reference signal. The reference signal is in this case in the form of the noise signal y(t) that is applied to the acoustic device 6, although it could also be a signal detected at the sound generator, and could be e.g. produced by a further sensor. A single point correlation is performed by multiplying these two signals together, with the signal from the generator 5 being time shifted by a variable delay ($\tau$) 10 set so as to take account of the transit time of the signal through the PAP line and patient airway, e.g. a delay is chosen that produces a maximum value for the cross-correlation.

It would also be possible to monitor attenuation in other manners, and the signal detected by the sensor could be directly reviewed and analysed without cross-correlation. However, the correlation of the two signals assists in the rejection of respiratory and environmental noise, and makes for a more robust system of measurement.

The output of the correlator 9 can provide a full or partial impulse response for the combination of the airway, PAP and measurement system, and this can be passed to suitable processing circuitry 11 to provide a patency signal by for example equating a characteristic of the impulse response, such as the size of a peak in the response, to the degree of patency.

The apparatus 1 may be calibrated by having a patient breathe through the nose whilst awake, with the mouth closed, and by setting a measured characteristic of the resulting impulse response, such as a peak, to 100% patency. If, during sleep, a reduction in patency occurs in the airway, the impulse response characteristic will change in value, e.g. a loss of peak height and the degree of change from the 100% calibration value may then be associated with a similar degree of patency change.

It will be noted that the present invention may not only determine simply that an airway is open or obstructed, e.g. by determining if a characteristic of the impulse response exceeds a threshold value, but may also determine a degree of patency, for example whether an airway is partially obstructed and to what extent, e.g. from the degree of change in a characteristic of the impulse response. Accordingly, it will be understood that the term patency may relate to both a simple consideration of whether or not an obstruction exists and also to the degree to which an airway is obstructed (or clear).

The determination of patency allows for various breathing events to be determined and monitored. For example, the apparatus may monitor apneic events, where the airway is completely obstructed and there is no airflow, and hypopneic events where the airway is only partially obstructed and there is reduced airflow. It may also monitor events associated with Upper Airway Resistance Syndrome (UARS), in which the airway may be partially obstructed, and where arousal may occur, but where these events are not regarded as apneic or hypopneic, e.g. because there is no decrease in blood oxygen levels. These events may be monitored and logged for diagnostic analysis and treatment assessment.

The patency determination may be used with other parameters to provide further determination of patient condition. For example, the apparatus 1 may include a sensor for determining airflow. This could take a number of forms, including an inline airflow sensor, a pressure sensor or a thermistor. In the apparatus shown, airflow may be determined by monitoring pressure at a location 12 within the mask 3. Airflow and patency may be used for example to determine hypopnea as opposed to apnea, and may be used to discriminate between a central apnea (the central respiratory rhythm generator does not activate the muscles of breathing) and an obstructive event (the central respiratory rhythm generator activates the muscles of breathing but a collapsed airway prevents inflow of air to the lungs). For example, no airflow and an obstruction would indicate an obstructive event, whereas no airflow and no obstruction would indicate a central event.

The patency output may also be used in the control of the PAP apparatus 2. Thus, the PAP device 2 may be operated according to detected respiratory events, and e.g. may provide a variable positive pressure based on the occurrence of an obstruction and/or on the degree of airway patency. For example, the PAP device could provide an increase in pressure when apneic or hypopneic events occur, and could decrease pressure when such events no longer occur. This could then provide variable control of the apparatus. The device 2 may also be an intermittent auto-titrating device that would stop the application of positive pressure when the airway is open (and e.g. allow a patient to breathe ambient air through actuation of a suitable valve arrangement or the like), and then revert to a PAP mode when an obstruction develops.

The present invention may be applied to any suitable respiratory assist device including any device that administers positive airway pressure, including CPAP and variants on CPAP. Thus, whilst CPAP may relate generally to all positive airway pressure devices, the devices may generally be categories as those that continuously apply a single pressure level to a patient, those that apply one pressure level on inspiration and a lower level on expiration (BiPAP), those that apply pressure on a demand basis (DPAP), and those that vary the pressure level and provide auto-titration (VPAP and APAP).

The present invention facilitates auto-titration of the positive pressure by allowing for servo-control of the respiratory assist apparatus so that it uses the patency feedback to determine a suitable pressure level for a patient that will keep the patient's airway open. This pressure level may be determined once for a patient, and that value then used in future treatment, or may be determined periodically, so that the pressure level is continually monitored and corrected.

The present invention may facilitate home diagnosis and home titration, without the need for expert intervention and without the need for expensive overnight sleep studies in sleep laboratories.

The present invention may also be used with other respiratory assist devices, e.g. ventilators and the like, so as to indicate a problem or the like with a patient, e.g. to alarm when there is an obstruction or other respiratory event.

It will be noted that the impulse response determined in this embodiment is not just of the airway, but is a combined response of the airway, the CPAP apparatus and the patency detection apparatus. Thus it includes for example the response of the CPAP line 4 and the filter 8. However, since the airway is the only significant variable in the combination, any changes in the response can be ascribed to changes in airway morphology.

Figure 8:
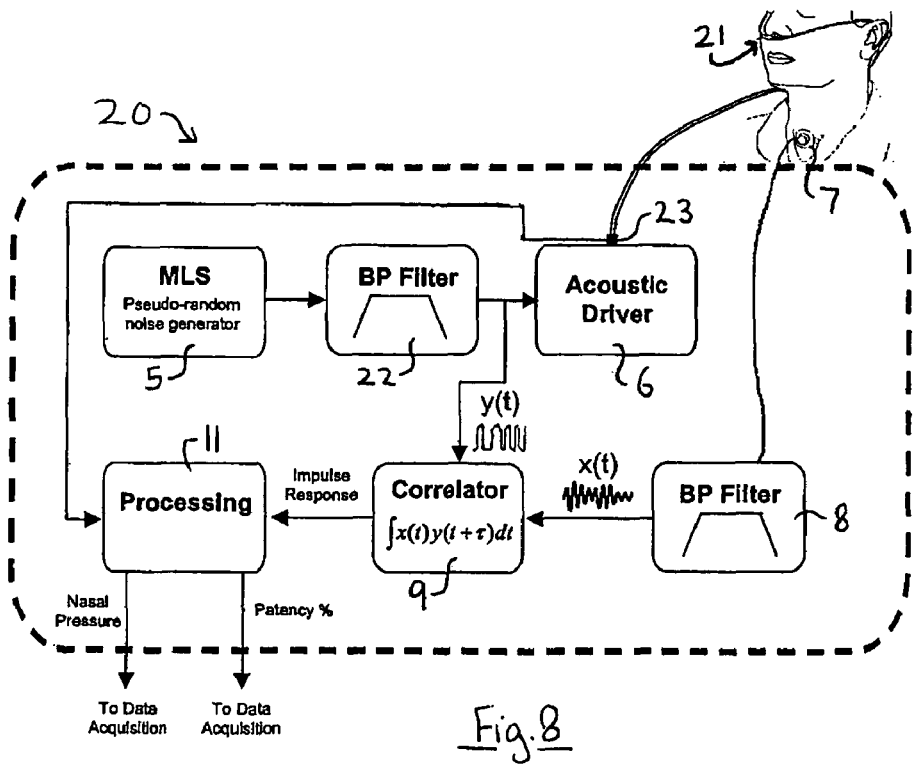
FIG. 8 is a schematic diagram of a patency detection system according to a second embodiment of the present invention.

FIG. 8 shows a second embodiment for a patency monitor in which the patency apparatus 20 applies the sound signal through a nasal cannula 21 and in which a band pass filter 22 is provided between the pseudo-random noise signal generator 5 and the acoustic driver 6.

The cannula 21 provides a useful method of applying the sound signal, which may be applied through the cannula prongs to one or both of the nares, or could alternate between the nares. It allows for good coupling of the signal into the nasal cavity and into the patient's airways.

The band pass filter 22 limits the applied input signal to a desired frequency band, and the two filters 8 and 22 are matched so that both pass the same frequency range. This again helps to remove unwanted noise and artefacts from the detected signal.

In this embodiment, the pseudo-random noise generator produces MLS noise. The MLS sequence has a repeat length such that its repetition is not distinguishable by the patient. For example, the sequence may be a 6-second MLS sequence with a mean value of 0.

The apparatus of this embodiment may be used for example in the diagnosis of sleep apnea, and may record apneic, hypopneic and other sleep-disordered breathing events over time. It may log the events and produce an apnea index (AI), an apnea hypopneic index (AHI) or a Respiratory Disturbance Index (RDI), which provide an average number of events per hour.

The apparatus may also include a pressure sensor 23, e.g. a microstructure pressure sensor, for providing nasal pressure data, e.g. to determine airflow. As previously described, this may be used with the patency data and any other variables of interest so as to provide further information on the nature of a breathing event, such as whether the event is central or obstructive. It may also be used to determine improper fitment of the cannula. It may be located in the cannula, or e.g. may be located at the coupling of the cannula to the acoustic driver 6.

The correlator 9 correlates the detected signal x(t) with the pseudo-random noise signal y(t). In this embodiment, however, the delay of the pseudo-random noise is swept over a range of values so that the complete impulse response of the system may be obtained.

The present invention uses sound in the audible frequency range, and may make use of sound having any suitable frequency characteristics. The frequency characteristics may be chosen so as to fulfil a number of criteria that have been found to be useful when applying a sound signal to a patient's airway.

Figure 15:
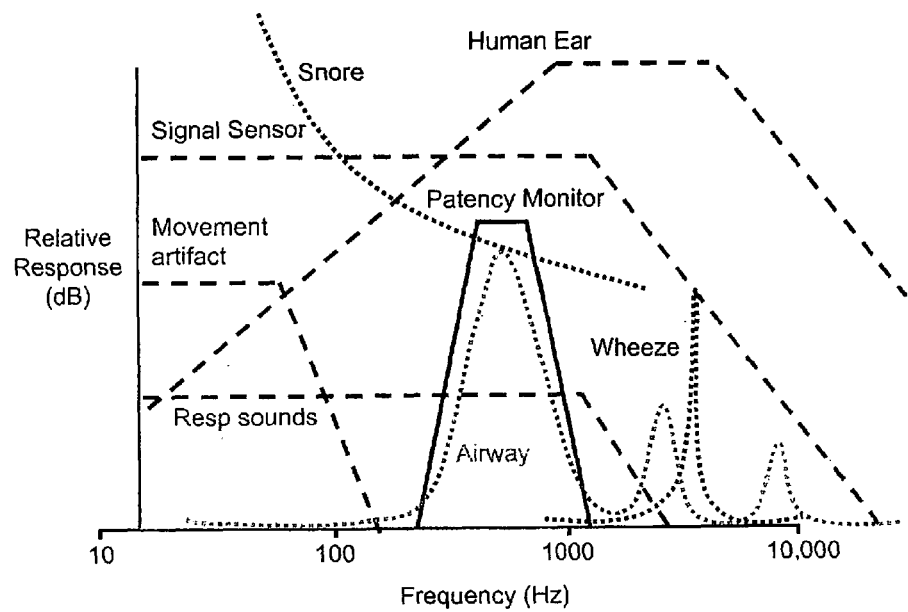
FIG. 15 is a diagram showing various relative frequency responses and frequency spectra of a range of interfering signals and of the human ear that may be taken into account by the present invention when determining the optimum frequencies of applied sound signals for the first, second, third and forth embodiment of the present invention.

One consideration is the degree of extraneous noise in the system. In this regard, it has been found that the use of a frequency range of between about 100 Hz and about 2 kHz is able to exclude a large amount of unwanted noise. Thus, as shown schematically in FIG. 15, the use of such a range can exclude sound frequencies associated with movement artefacts, as well as a good deal of the lower frequency components of snoring that tend to be large in amplitude. It can also exclude wheezing noise and other breathing noise.

In another consideration, the human ear is particularly sensitive to sound in the 1 kHz to 5 kHz range. Exclusion of frequencies in this range allows for the use of higher applied sound signal levels, and thus improves the signal to noise ratio.

Signal to noise ratio can be further improved by choosing a band of frequencies for the injected sound that is centred on one of the naturally occurring resonant frequencies associated with the airway that occur between 500 and 2000 Hz.

Further, a problem with monitoring patency during sleep can be the opening and closing of the mouth, which may affect the transmission characteristics of the airways and adversely impact upon the patency measurement. Nonetheless, it has been found that it is possible to find airway resonances between 600 and 800 Hz that can facilitate the transmission of an applied sound signal centred at these frequencies without being overly perturbed by mouth opening and mouth closing events. It is thought that these stable resonances are "tracheal" resonances, although the present invention is not limited by this conjecture.

It has been found that limiting the applied signal bandwidth is also beneficial, although it has been found that bandwidths narrower than about 150 Hz produce sounds having an unpleasant tonal quality that can be perceived by the subject under examination. Accordingly, it is preferred to use bandwidths wider than 150 Hz.

Although a wider bandwidth would have the benefit of less noise induced fluctuation in the system's impulse response for a given noise/signal ratio, it is preferable to constrain the bandwidth to less than 250/300 Hz, as a wider bandwidth increases the perceived loudness of the applied signal to the patient (for a given power level), and the ability to increase the applied signal strength without causing patient discomfort (by using a narrower bandwidth) has been found to be generally of more significance to the achievement of a good signal to noise ratio than is the use of a wider bandwidth to reduce fluctuations in the system's impulse response.

Wider bandwidths may be feasible when the patency monitor is used with CPAP or other respiratory apparatus, as the turbulent flow induced noise made by the apparatus will generally mask any injected noise that the patient may perceive from the patency apparatus, and for example a bandwidth of about 1000 Hz with a frequency range of about 500 to 1500 Hz has been used successfully in such a system.

It will be understood that while the above frequency and bandwidth ranges are optimal for use in adults for example, they are not limiting on the present invention, which may be used with any suitable signals in the audible frequency range.

Figure 9:
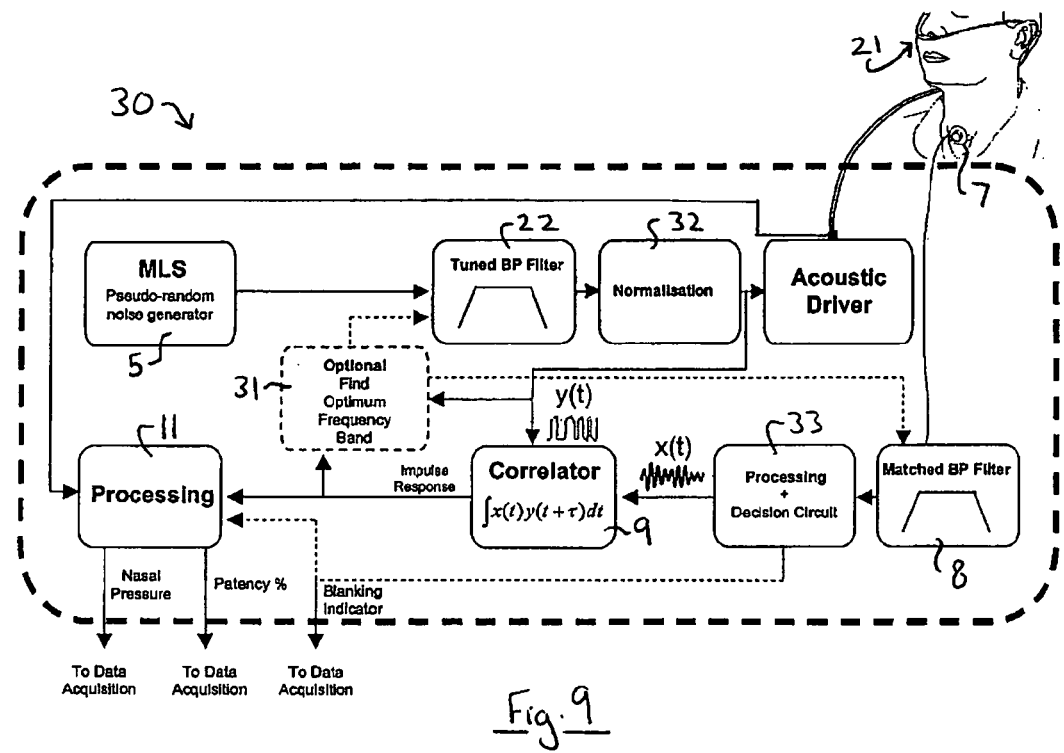
FIG. 9 is a schematic diagram of a patency detection system according to a third embodiment of the present invention.

FIG. 9 shows a modification of the apparatus of FIG. 8. One aspect of the modified apparatus 30 is that the band pass filters 22 and 8 are tunable through a tuning control 31. This allows the applied signal to be tuned to an optimum frequency band for the particular patient under investigation.

Thus, the tuning control 31 may receive the output of the correlator 9, and may vary the centre frequency and signal bandwidth so as to optimise the impulse response in some manner.

In one preferred embodiment, a default signal, with a bandwidth targeted to ensure that resonances will be captured within it, e.g. a 600 to 800 Hz signal is applied to a patient's airway, a frequency response is obtained (e.g. by an FFT of the correlator impulse response), and the frequency of airway resonance is determined. The bandpass filters 22 and 8 are then tuned to this frequency This thus allows for optimal transmission of the applied sound signal through the airway as discussed above.

Both the applied signal band pass filter 22 and the detected signal band pass filter 8 are tuned by the tuning control 31.

In one embodiment, the band pass filter 22 is set to a default range of 500 Hz to 800 Hz, which can then be tuned as required, i.e. it is initially at a central frequency of about 650 Hz, with a bandwidth of about 300 Hz.

The applied sound signal may for example be centred on a resonant frequency of the upper airway, e.g. a resonance of the trachea, and the tuned filter 22 may be altered so as to provide an applied sound signal centred on one such resonance.

Again, in this embodiment, the noise signal may be based on an MLS sequence that is of suitable duration so as to minimise the perception of the applied signal to the patient. With a long duration sequence, it may mean that the impulse response of the applied sound signal can only be determined after long time intervals. In the present embodiment, however, the MLS sequence is split into packets that are each then normalised in a normalisation circuit 32, e.g. to the RMS value of the sequence. This then allows the impulse response and so patency to be determined at a higher rate, e.g. once every sampling packet. A sampling block/packet may e.g. be of about 0.1 seconds in length.

The apparatus of FIG. 9 also includes a processing circuit 33, which may be termed a "blanker" circuit, for monitoring the detected sound signal from the sensor 7 and for rejecting high amplitude interfering signals that may be associated with vocalisation or snoring.

In one embodiment, the processing circuit 33 compares the detected signal with a threshold value and rejects data that exceed that threshold. This can prevent data associated with snoring, patient alarms or the like from passing to the correlator and patency determining circuits, where they could cause erroneous patency indications.

The processing circuit 33 may also or alternatively compare the detected signal level with an adaptive threshold that changes its value based on the detected signal level. Thus, the adaptive threshold may be set to a value based on some multiple of the RMS value of the detected signal, e.g. four times the RMS value. This helps to reduce the effects of high amplitude transient noise signals, whilst adjusting to continuous long-lasting changes in background noise. The processing circuit 33 may use both a set relatively high threshold e.g. that will activate on snoring but not sounds associated with breathing, and a generally lower adaptive threshold, e.g. for transient noise signals.

The processing circuit 33 may reject an entire packet, e.g. a 0.1 second block, if any of the packet data exceeds a threshold level. In an alternative embodiment, the processing circuit may set data in the packet that exceed a threshold value to a lower value, e.g. to a zero value, and then pass the modified packet data to the correlator 9. For example, a packet of 0.1 seconds may have 4410 samples within it (i.e. the detected sound signal is sampled at 44100 samples a second), and it may be that 30% of these are above the threshold, in which case these 30% are set to zero amplitude.

When the processing circuit 33 operates to blank signal data, it may further modify the patency output to account for this. For example, the processing circuit 33 may cause the patency determining circuit 11 to hold a previous patency level when a packet is rejected. Where packet data have been reduced in value, e.g. to a zero value, the patency level may be calculated based on the modified packet. In this case, the resulting patency value may be compensated based on the amount of sampling data that was modified, e.g. the patency signal may be increased by an amount proportional to the amount of data modified.

In another embodiment, instead of holding a previous patency level, a predictive algorithm is used to substitute the patency of a blanked sample with a predicted value based on a weighting of previous samples.

In a further embodiment, blanking is achieved by taking the fast Fourier transform of the detected signal and comparing the frequency coefficients with a fixed threshold or a variable threshold e.g. based on frequency coefficients of the applied sound signal, e.g. as determined by the filter coefficients of the signal's FFT. For example, a packet may be rejected if frequency components exceed a threshold or the frequency components may be attenuated if a magnitude threshold is exceeded. The inverse fast Fourier transform may be used to reconstruct the detected signal.

Figure 10:
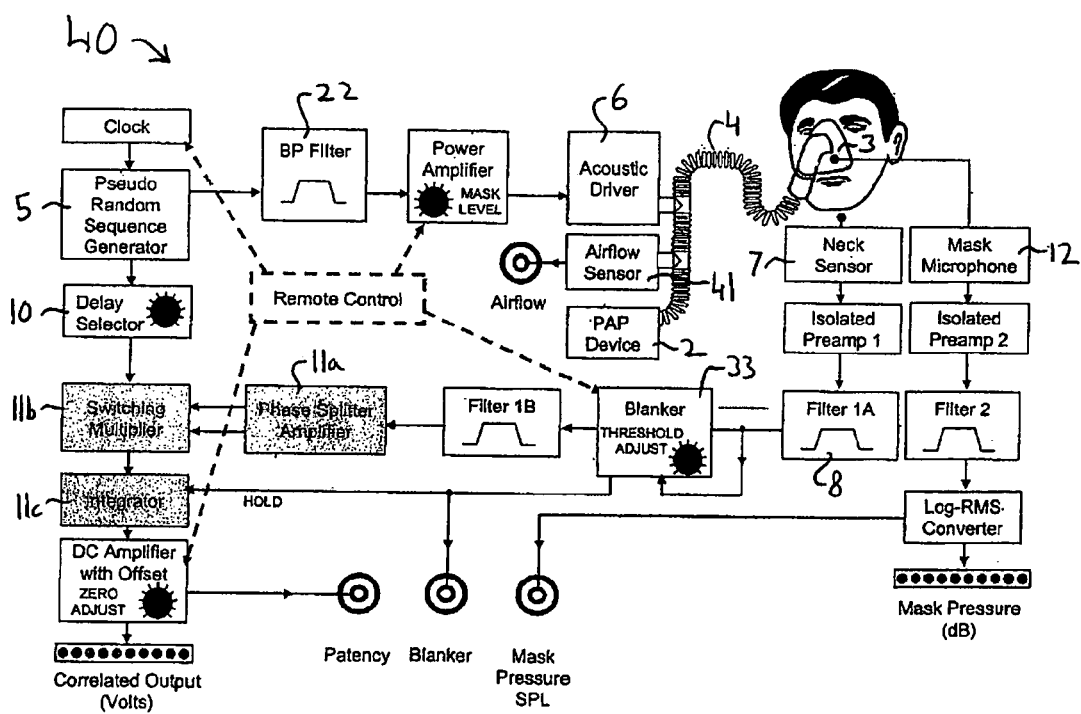
FIG. 10 is a schematic diagram of a patency detection system according to a fourth embodiment of the present invention.

FIG. 10 shows a further embodiment, in which a patency monitoring system 40, similar to that in FIG. 7, but with blanking circuitry similar to that of FIG. 9, is applied to a PAP machine 2.

This embodiment also includes an airflow sensor 41, which can detect the airflow in the PAP line 4. This may be used with the patency values to discriminate central and obstructive apnea, as previously discussed with regard to the airway pressure sensors 12 and 23.

In any of the above embodiments, further sound detectors may also be included, e.g. to provide a second reference detection signal, to detect extraneous noise and/or to provide noise cancellation.

For example, the outputs of two or more detectors may be added, subtracted or averaged or the signal that is most optimal may be used for patency determination. The outputs may also be used to provide independent processing, and may be used to determine patency in different parts of the airway.

Also, a detector may monitor extraneous events to allow for noise cancellation, and may e.g. be placed remote from, near or within the neck sensor. The signal may be used with an adaptive noise-cancelling algorithm that aims to minimise the mean square error. A further embodiment may allow for noise cancellation based on a scaled addition or substraction of two detected signals.

In the above embodiments, the sound detector 7 is preferably mounted in the supra-sternal notch, as this provides for minimum attenuation of signal. The detector could however be placed in other positions, e.g. elsewhere on the neck, on the anterior or posterior surfaces of the chest, or on the abdomen.

In another possible embodiment, the patency signal may be passed through a low pass filter, e.g. a filter with a time constant of 2 seconds, so as to reduce further noise artefacts and the like.

The coupling of the input sound signal into the airways may take any other suitable form and for example the nasal cannula could be replaced by a mask, nasal plugs or any other suitable coupling.

The output of the processing circuitry 11 and the pressure and airflow sensors 12, 23, 41, as well as information as to when blanking of data samples occurs, may be stored and displayed in any suitable manner, and may be combined with other patient data as required.

The apparatus may be configured to output a breathing disorder index, e.g. an Apnea Index (AI), an Apnea Hypopnea Index (AHI) or a Respiratory Disturbance Index (RDI). These relate to the average number of respiratory events per hour, e.g. apneic and/or hypopneic events, and the apparatus may discriminate and record these events over time to provide the desired index.

The present invention may be applied to sleep-disordered breathing devices in general. It may for example provide respiratory assist apparatus in general with a patency signal that may be used to control the apparatus e.g. in a feedback manner. For example, the patency apparatus may be used in positive airway pressure devices in general, such as bi-level positive airway pressure (Bi-PAP) apparatus, intermittent apparatus and auto-titrating positive airway pressure (APAP) apparatus.

The patency signal may be used to control the application of respiratory assistance, e.g. when to apply a positive pressure, and the degree of respiratory assist, e.g. the level of positive pressure. For example, the detection of an obstruction or decrease in patency may cause a positive airway pressure device to begin to apply pressure or to increase the applied pressure, whilst an increase in patency may cause the device to stop the application of pressure or reduce the applied pressure.

The present patency signals combined with other patient parameters, such as airflow, may be used to discriminate between central and obstructive events. This can be useful with respiratory apparatus to ensure that pressure levels are appropriate, e.g. so that positive pressure is not used in an attempt to alleviate central apneas. Indeed, the present patency apparatus can minimise the inappropriate application of positive pressure, and so may help to prevent damage to the respiratory system. This may be especially useful with neonates.

Although discussed mainly in relation to sleep-disordered breathing, the present invention has other applications also. For example, the apparatus may be used to monitor the airway patency of an infant or incapacitated or unresponsive adult, e.g. during anaesthesia. The present invention may also be applied in the field of ventilation generally, and to any suitable respiratory assist device, treatment or therapy. The apparatus may for example include an alarm that is activated when a respiratory event is detected.

Figures 11A, 11B:
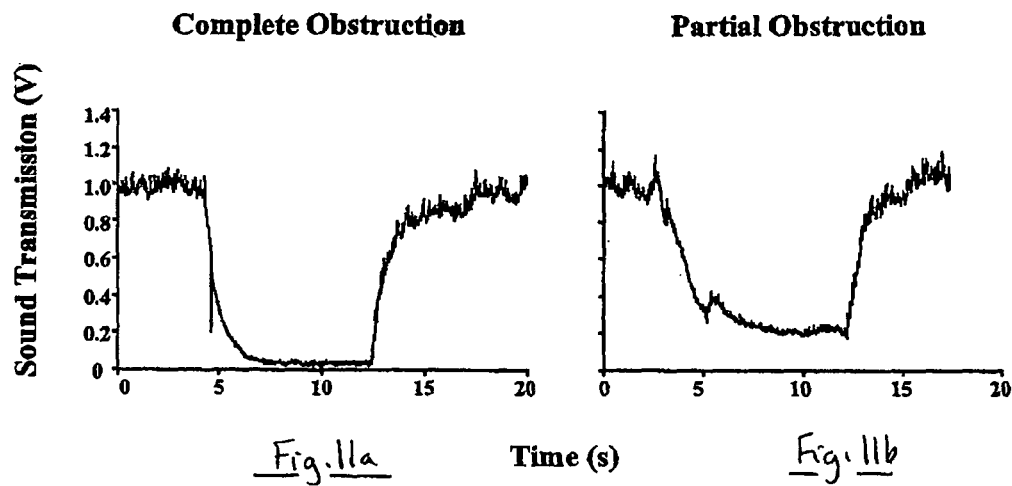
FIGS. 11a and 11b are graphs illustrating the effect of airway closure on the transmission of sound from its point of injection at a subject's nostrils to the thoracic inlet at the notch in the sternum located at the base of the neck.

FIGS. 11a and 11b show sound transmission through the upper airways, as measured with a patency system similar to that of FIG. 7, in which the attenuation of an applied sound signal input into the mask 3 is measured with signal sensor 7.

When the larynx is voluntarily closed (corresponding to a complete obstruction of the airway), transmission falls from a level of 1 volt to zero volts, thereby indicating loss of the signal that was transmitted into a face mask and measured at the base of the neck. When the subject partially closes the larynx, the output of the patency detector falls towards zero and indicates partial obstruction.

Figure 12:
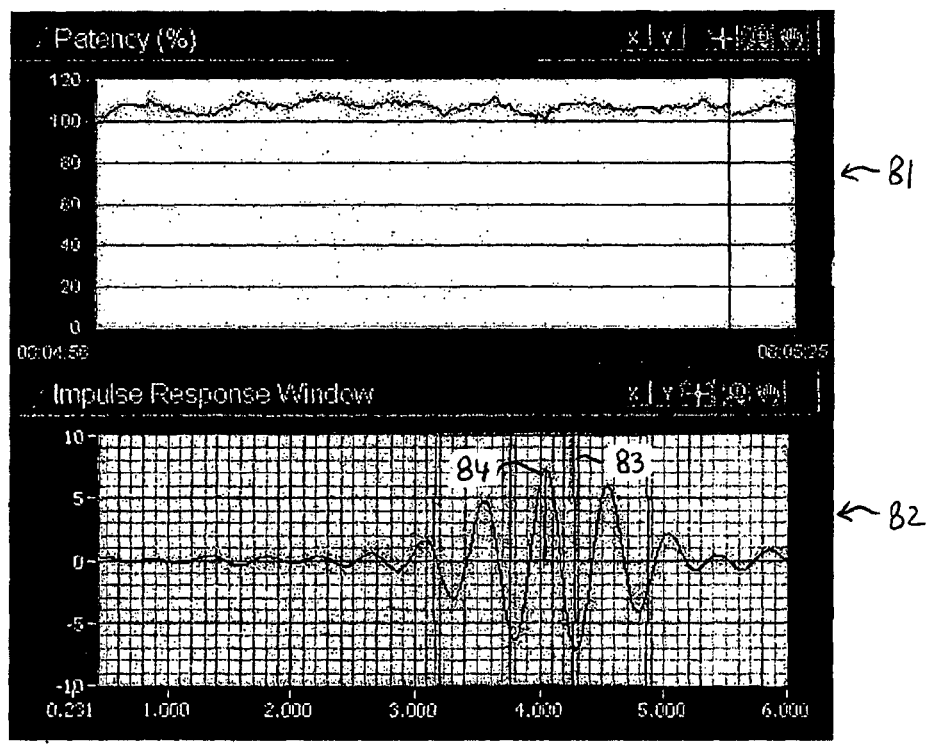
FIG. 12 shows a screen shot of an impulse response and patency display for a patency monitor constructed in accordance with the third embodiment.

FIG. 12 shows a screen shot of patency and impulse response windows 81 and 82 respectively that may e.g. be obtained from a system such as is shown in FIG. 9. Thus, the impulse response signal in window 82 is updated for every packet of data, e.g. a 0.1 second packet, and the patency for that impulse response is determined and displayed as a data point in the patency window 81.

The patency may be determined in a number of ways from the impulse response. In one embodiment, a window 83 of the impulse response is selected, and the main peak 84 of the impulse response within this window is found and tracked. Thus, the main peak 84 of each impulse response is determined, and patency is determined by the height of the main peak.

To calibrate such a system, the patient may be asked to breathe normally through the nose with the mouth closed, and the peak amplitude of the impulse response may then be scaled to 100%. During sleep or the like, as patency decreases or increases, the amplitude of this peak will change accordingly to provide a percentage patency measurement.

In an alternative embodiment, a window of the impulse response is selected, and the main peak of the response is found within this window. The point at which the peak occurs is then monitored. In this embodiment, if the location of the main peak changes, e.g. due to minor changes in the airway, the impulse response amplitude at the original peak location, and not at the peak itself, is determined. Again, the amplitude at this point may provide a determination of patency.

Other patency measures are also possible. For example, multiple peaks of the impulse signal may be monitored, and e.g. the results averaged. Other values or characteristics of the response, such as an RMS, mean or integrated value, may also be used to determine patency, and a frequency response may be used instead of the impulse response, e.g. by applying a fast Fourier transform to the impulse response and monitoring changes in the frequency spectrum.

Figure 13:
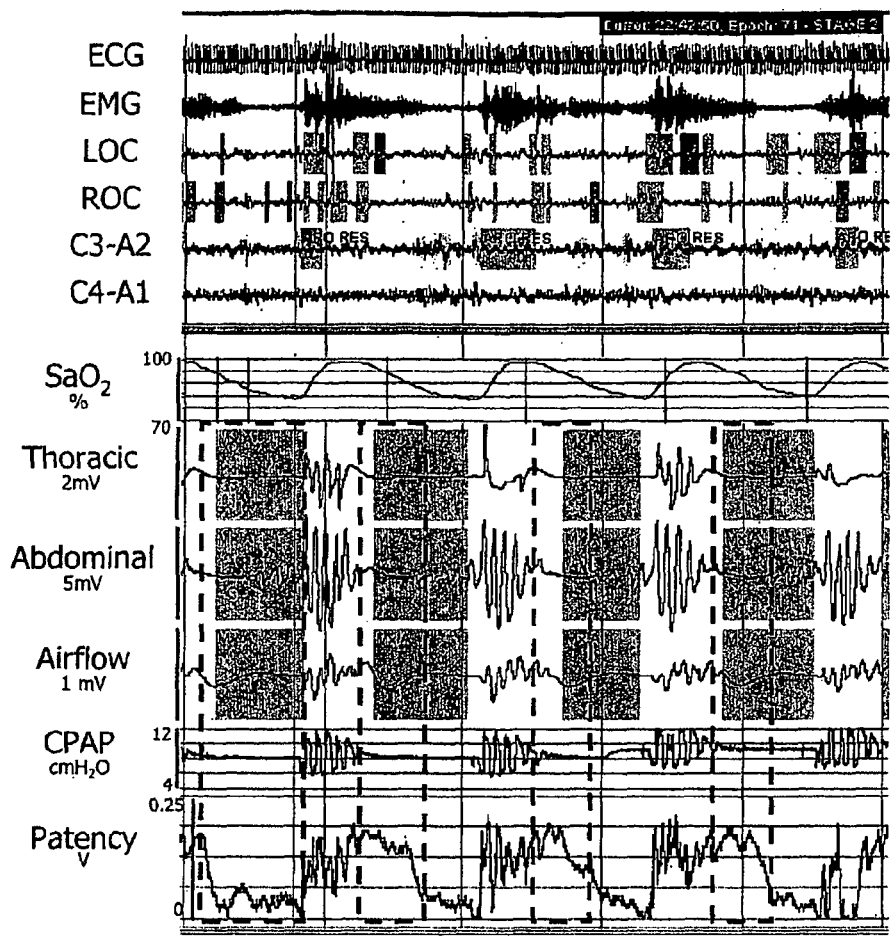
FIG. 13 shows polysomnography data and patency data obtained by a patency monitor constructed in accordance with the first embodiment and collected from an adult subject with OSA.

FIG. 13 is a polysomnography record for a patient undergoing clinical evaluation for a suspected sleeping disorder, e.g. obstructive sleep apnea, showing where a mixed apnea condition (MxA) has occurred. The measurements taken may include e.g. electrocardiogram (ECG), submental muscle activity (EMG), left and right oculograms (LOC,ROC), electroencephalograms from the C3-A2 and C4-A1 positions on the scalp, arterial oxygen saturation ($SaO_2$), thoracic and abdominal movements, airflow at the nostril/mouth, and the level of continuous positive airway pressure (CPAP) delivered to the face mask. It will be noted that when the polysomnography analysis indicates that the patient has a mixed apnea (MxA), which is a combination of central and obstructive apnea, the patency signal falls to zero.

The present invention may be used with any of these standard measurements to provide a more accurate overall assessment of a patient's condition.

Figure 14:
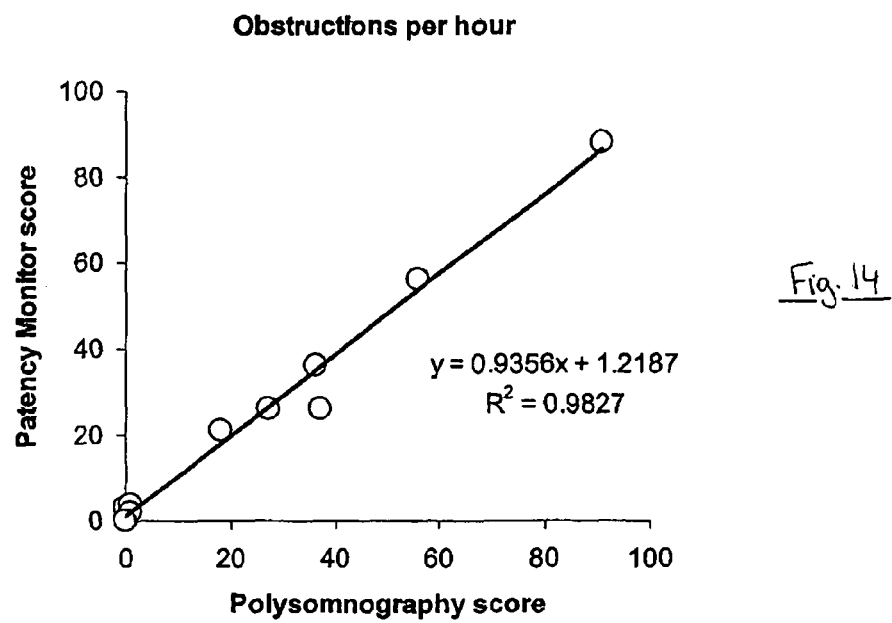
FIG. 14 is a graph comparing a polysomnography score determined using an accepted scoring protocol to a score based on a patency test using a patency monitor in accordance with the first embodiment of the present invention.

FIG. 14 shows a graph of polysomnography scored patency against patency scores determined according to an embodiment of the present invention according to FIG. 7. As can be seen, the patency and polysomnography scores correlate well with one another.

As discussed previously, FIG. 15 is a diagram of general frequency components of various possible extraneous noises that are to be taken account of, e.g. snoring, wheezing, other respiratory sounds and movement artefacts, together with the frequency response of the human ear and an electro-acoustic transducer that may form the sensor 7. Preferably, the input signal frequencies are chosen so as to lie within an area that excludes significant amounts of these extraneous sounds.

Figure 16:
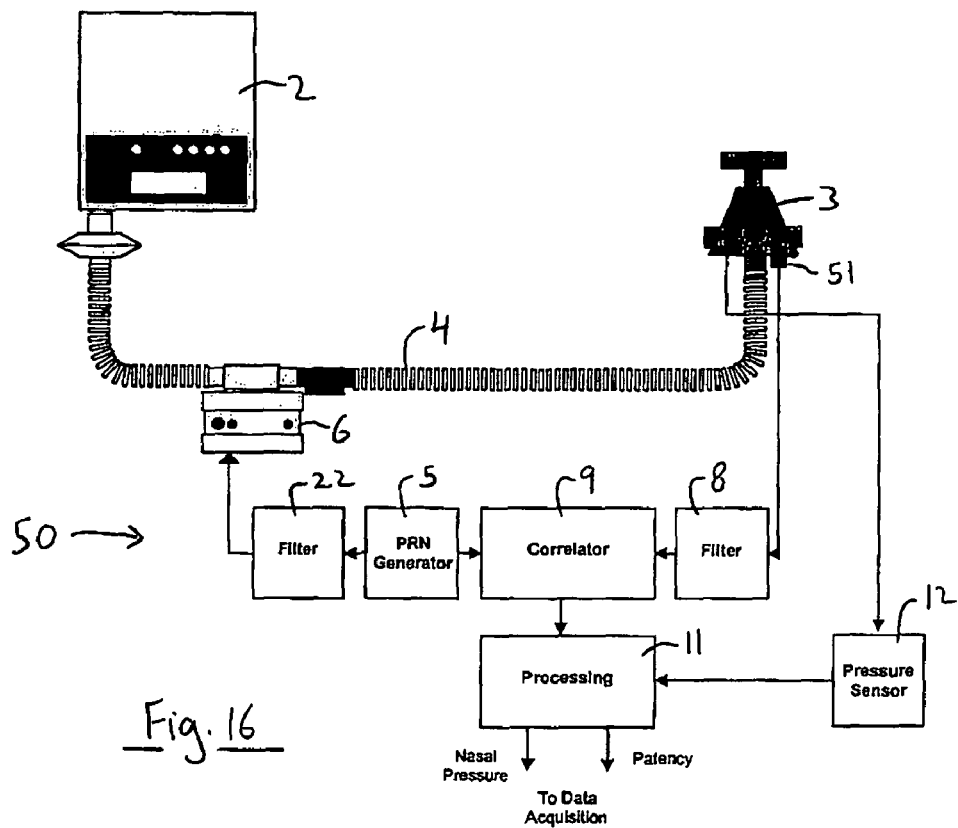
FIG. 16 a schematic diagram of PAP apparatus utilising a patency detector according to a fifth embodiment of the present invention.

FIG. 16 shows a further embodiment of the present invention, in which patency determining apparatus 50 is shown used with a respiratory assist device 2, e.g. a positive airway pressure device, such as a CPAP, BiPAP or APAP device.

In this embodiment, as before, sound is injected by an acoustic driver 6 into the respirator line 4, and a response to the sound signal is again determined by detecting the interaction of the sound signal with the airway. Patency is then again determined by monitoring changes in the response.

In the present embodiment, however, the response is determined by reflected sound detected at a mask microphone 51, rather than sound detected at e.g. the base of the throat. Thus, in this embodiment, the sound signal received by the mask sensor 51 will consist of the applied signal as well as a signal resulting from the complex interaction of the applied signal with the airway, Reflections may occur from points in the buccal or nasal cavities, in the pharyngeal regions, in the laryngeal region and in the tracheal region, as well as in the first few bronchial generations of the lung.

In the event of a change in patency of the airway, e.g. an obstruction or partial obstruction in the airway, the signal recorded by the sensor 53 will alter. Changes in this signal may be monitored to indicate patency, and again may relate to variations in the signal shape and/or strength, e.g. due to absorption, transmission and reflections from various sites along the airway and also due to interference between these paths.

Again, the patency information may be combined with other information such as mask pressure from pressure sensor 12 or airflow from an airflow sensor, and may be used to servo control the respiratory assist device 2.

Figure 17:
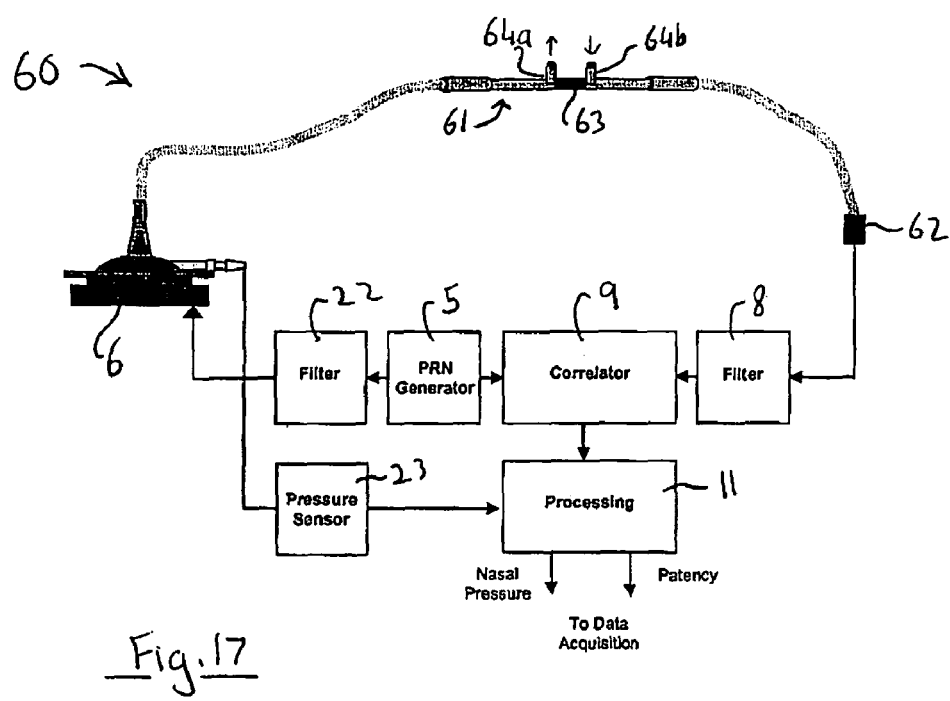
FIG. 17 is a schematic diagram of a patency detection system according to another embodiment of the present invention.

FIG. 17 shows a further embodiment of the present invention, which shows patency apparatus 60 that also uses a reflectance technique, but in this case the sound signal is applied through a nasal cannula 61 that is coupled with an acoustic driver 6 at one end and with a microphone 62 at the other end. The cannula 61 includes an acoustic blockage 63 between the nasal prongs 64a,64b, so that sound introduced by the acoustic driver 6 travels into the airway of the patient through nasal prong 64a and one of the nares of the patient, and reflected sound is detected by the microphone 62 via the other of the nares of the patient and nasal prong 64b.

Figure 18:
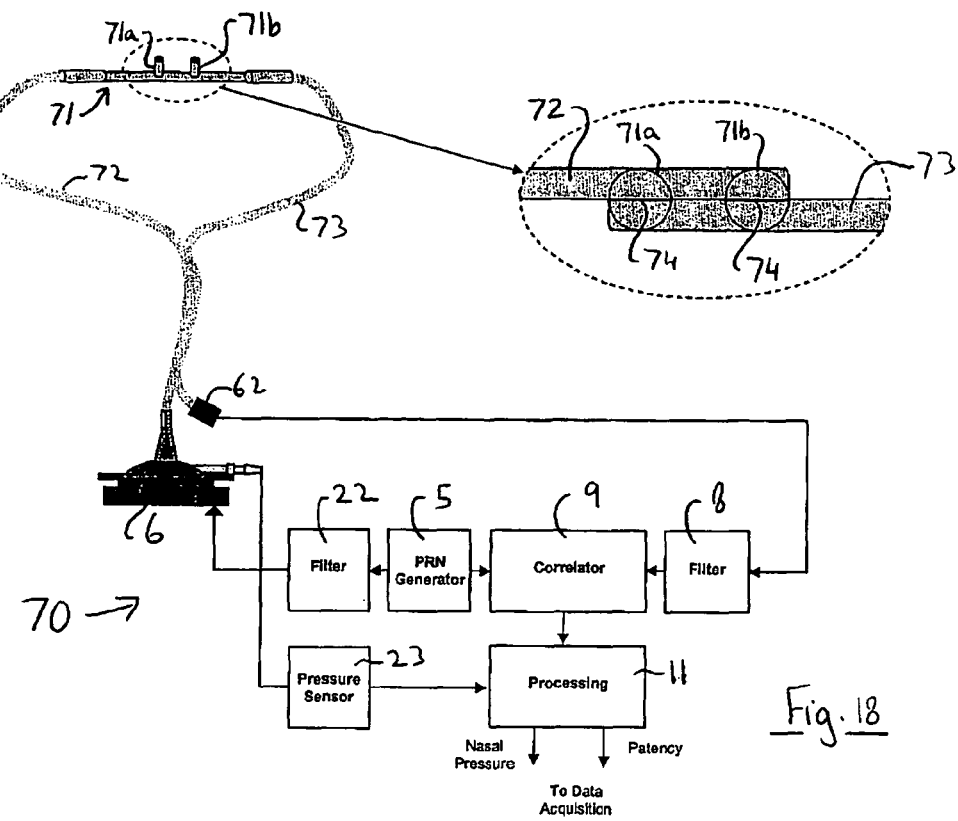
FIG. 18 is a schematic diagram of a patency detection system according to another embodiment of the present invention.

FIG. 18 is a modification of the FIG. 17 arrangement. In this apparatus 70, a dual lumen cannula 71 is used, with the acoustic driver 6 coupled to one lumen 72 of the cannula 71 and the microphone 62 coupled to a second lumen 73. In this embodiment, sound is input to both of the nares through both nasal prongs 71a, 71b, and the response is also detected from both nares, again through both prongs 71a, 71b (in a dual lumen cannula, each nasal prong 71a, 71b includes a divider 74 along its length, so that one half of each prong connects with one of the two lumens 72,73). Other arrangements are also possible, e.g. a separate acoustic driver 6 and detector microphone 62 may be associated with each prong, and each may be used to independently apply and receive sound signals.

The sound signal input and the processing of the detected response in the embodiments of FIGS. 16 to 18 may take forms similar to those discussed above in relation to the other embodiments. In one embodiment, for example, the magnitude of the reflected energy may be monitored, e.g. a magnitude of the impulse response, and this may be translated to a degree of patency or compared with a threshold value so as to indicate a respiratory event.

Again, instead of using the impulse response, a frequency response may be derived, e.g. by a FFT of the impulse response.

In one embodiment, a change in the signal profile, e.g. the energy profile of the signal may be monitored. The signal profile may be compared to a reference patent profile and/or an obstructed profile to determine an obstruction, or portions of the signal profile may be compared with one another.

Thus, the detected signal profile will relate to the applied signal through a complex combination of attenuation, transmission, refraction and reflection from various sites along the airway, and, although no reliance is made on the exact nature of these interactions, it will be understood that a change in state of the airway will alter the response profile, and obstructions at different parts of the airway will affect different portions of the response signal in different ways. More specifically, portions of the signal response associated with the airway above and below an obstruction may alter in a different manner from one another.

Therefore, in one embodiment, portions of the signal response may be compared to one another to determine patency, and a comparison may be made between portions of the response signal associated with response from above an obstruction and portions of the signal associated with response from below the obstruction. This may be achieved, e.g. by comparing the signal energy of two or more portions of the signal, e.g. their average energies, e.g. their rectified amplitudes.

One example of this is in the determination of a sub-glottal portion of the signal response and a supra-glottal portion of the response. In this example, a patient may be asked to voluntarily obstruct their airway e.g. by a sustained swallow, to facilitate calibration between a fully patent and an obstructed airway. The signal change from a fully patent airway to an obstructed airway may be used to identify portions of the signal that correspond with supra-glottal reflections and sub-glottal reflections. These portions may be windowed for subsequent monitoring.

A ratio of the average energy in the two regions may be determined for the fully patent and obstructed states. Changes in the ratio may then be monitored and correlated with the degree of patency of the airway.

Also, an obstruction or partial obstruction may be identified from a change in the signal profile, e.g. a shift in the energy profile. With adequate temporal resolution, signal windows may be determined from this change, and may be positioned over regions of the signal corresponding to portions of the airway that are above and below (proximal and distal to) an obstruction or partial obstruction. The average energy or some other characteristic of the windows may then be determined and compared with each other to determine patency.

Monitoring may occur with both time and frequency domain signals, e.g. an impulse response or frequency response. In the frequency response, a relative change in amplitudes between various signal frequencies may be monitored.

Figure 19:
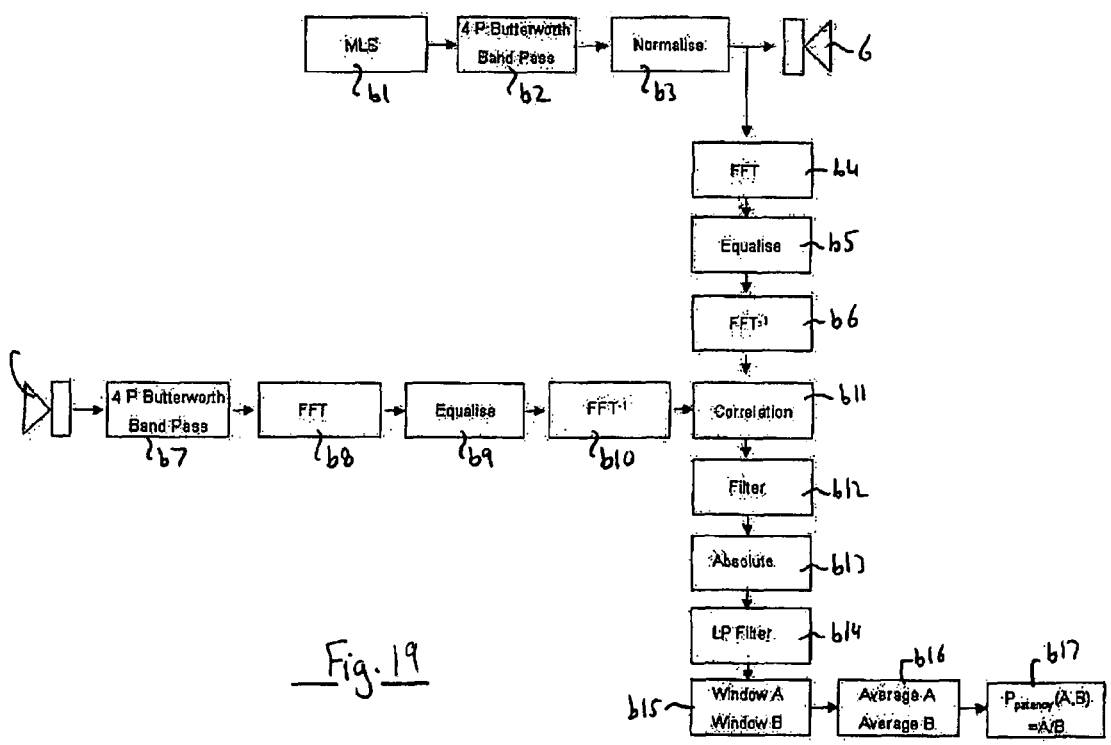
FIG. 19 is a block diagram of an implementation of the present invention.

FIG. 19 shows a block diagram for one implementation of this embodiment. Thus, in blocks b1-b3 an MLS signal is generated, bandpass filtered and normalised to provide signal packets as previously discussed, and the resulting signal is applied to an acoustic driver 6. The driver signal is also fed to a correlation block b11 to act as a reference signal for cross-correlation with the response signal detected by the detector microphone, e.g. 53 of FIG. 16 or 62 of FIG. 17, after the detected signal has been band passed filtered in block b7.

Before correlation, the driver and detected signals are normalised over the entire frequency range by conducting a fast Fourier transform (FFT) at b4,b8, equalising the frequency amplitudes at b5,b9 and by then conducting an inverse FFT at b6,b10. This modifies amplitude information whilst retaining phase information. The effect of the band pass filters b2 and b7 on the system's impulse response is thus removed. These steps may also be applied to other embodiments, and although not essential, assist with noise immunity.

The impulse response output by the correlator block b11 is then filtered at block b12, e.g. by either an integration or a linear filter, and the absolute value of the response is then determined in block b13 in order to facility calculation of the signal energy. The rectified signal is then smoothed by filter block b14, and a pair of windows is applied to the resulting signal at block b15. The windows correspond to the supra and sub glottal region reflections, and their location may be determined during initial calibration. The average energy of each window is then determined in block b16, and patency is determined in block b17 based on e.g. a ratio of the two averaged window energy values.

The applied sound signal may advantageously have a frequency bandwidth of between about 100 HZ to 10 kHz. The use of higher frequencies tends to provide higher resolution. The frequency bandwidth may be further limited over the frequency range where there is greatest variability between a fully patent and obstructed airway. Experimentally this has been found to be around 1 kHz to 3 kHz when using apparatus in accordance with FIG. 16, and 2 kHz to 3 kHz when using apparatus in accordance with FIG. 17. The frequency range may be further modified to avoid the effect of mouth open vs. mouth closed.

It will be understood that the above frequency bandwidth ranges are not limiting on the present invention, which may be used with any suitable signals in the audible frequency range.

Figure 20:
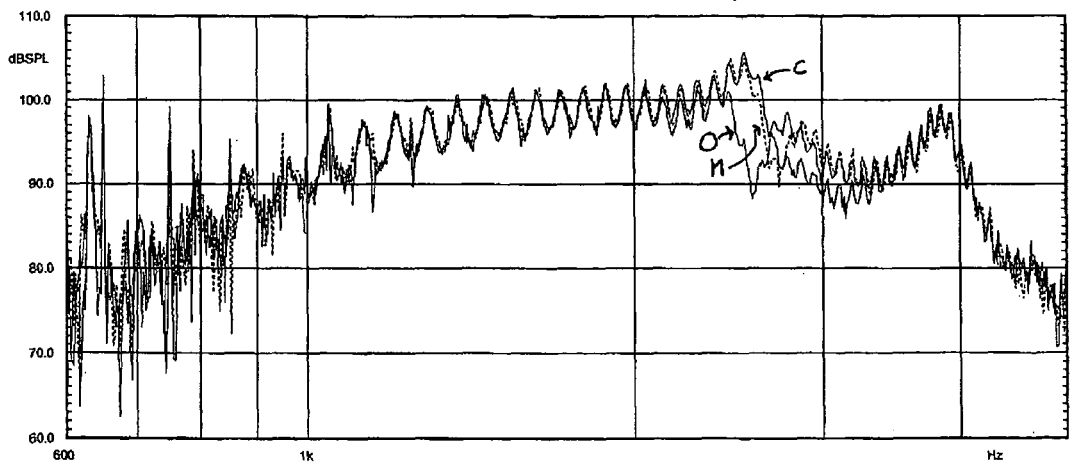
FIG. 20 is a frequency response for an experiment using apparatus in accordance with FIG. 16.

FIG. 20 is a frequency response for an experiment using apparatus in accordance with FIG. 16, in which an MLS sequence was applied to an airway. The result shows a significant change at around 2500 Hz for glottis open and glottis closed frequency responses (O) and (C) respectively, as well as a further change for glottis open and mouth open (M). This suggests that the present embodiment may be used to distinguish additional airway states, such as a mouth open state. Thus, comparisons of normal patency signal profiles with the profiles of a monitored subject can be used to determine a patency condition.

Figure 21:
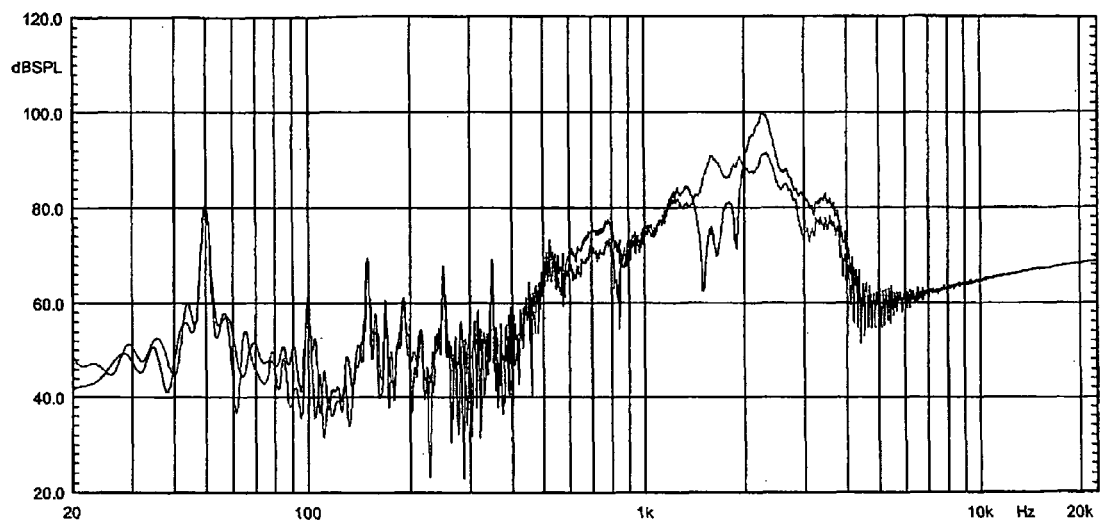
FIG. 21 is a frequency response for an experiment using a split cannula as in FIG. 17.

FIG. 21 is a frequency response for an experiment using a split cannula as in FIG. 17, in which a MLS sequence was applied to an airway. Again, the effect of opening (O) and closing (C) the glottis is evident in the frequency domain. As can be seen in this experiment, a portion of the frequency profile has enlarged amplitudes, whilst a portion has reduced amplitudes. A comparison of these two portions (e.g. a ratio of the signal energy) may therefore give an indication of patency.

Figure 22:
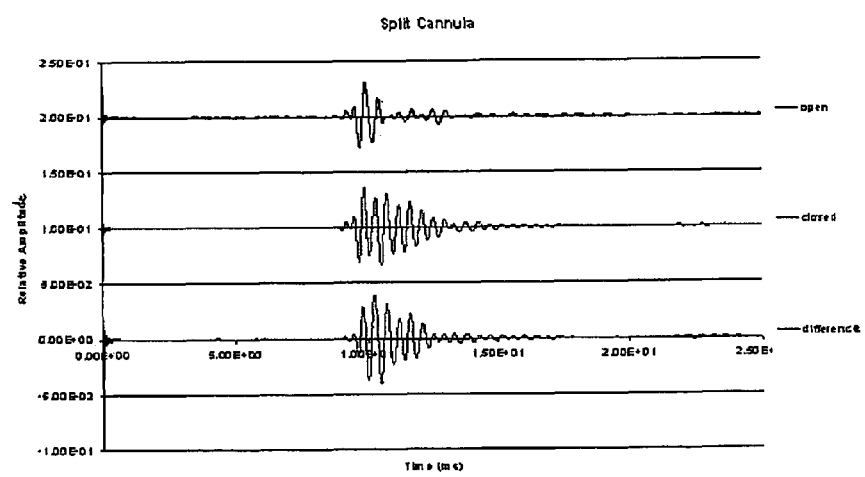
FIG. 22 is a time domain response corresponding to the frequency response of FIG. 21.

The time domain response corresponding to the FIG. 21 frequency response is shown in FIG. 22. As shown, an obstruction or closure of the airway results in a significant change in the time domain profile. The response for the open airway is most likely dominated by the path representing a direct transmission through the upper airway. The closed response also identifies a reflection caused by the obstruction. This is highlighted by the difference trace which represents the difference between the open and closed glottis signals. As shown, this is a slightly delayed response representative of the time of flight from the obstruction site, and hence can be used to determine the location of the obstruction.

One advantage of the reflectance system is that it does not require sensors to be attached to the subject under examination. and can be implemented using only the standard CPAP mask 3, nasal cannula 61 or the like, with no external body detectors (although it would be possible to use a detector attached to the subject, e.g. in the nose or mouth region, e.g. on a cheek).

The detectors in the reflectance techniques may also be less affected by noise than the use of a microphone attached to the body. In addition, the level of applied signal can be significantly reduced when compared to a transmissive technique.

As well as indicating that an obstruction exists or the degree of an obstruction, the present invention may also provide information about the position of an obstruction. For example, if a pulsed sound signal is applied to the airway, a time of flight calculation may be used to determine a reflection site associated with an obstruction.

Also, obstructions originating in the upper portion of the airway may be associated with an increase in higher frequency components of the detected signal whilst an obstruction occurring in the lower portion of the airway may be associated with an increase in lower frequency components of the detected signal. This results from a change in the resonant properties of the airway, and may be used to determine an obstruction. Both frequency information and phase information may also be used to provide an indication of position of the blockage.

It should be noted that the impulse response and frequency response of all of the embodiments relate not only to the airway, but to the combination of the airway and the measurement system, e.g. the path from the acoustic driver to the airway, the microphone and the various electronics. This is not problematic as the airway is the only significant variable in the combination, any changes in the response can be ascribed to changes in airway morphology. Also, the system can as discussed above be suitably calibrated for an open and closed airway for a patient, so as to provide a reference for determining patency measures.

Both transmission and reflectance techniques may be used together to provide a patency determination, and e.g. to have a detector both at the throat and at a nasal mask or cannula.

A first peak or peaks in the impulse response of a reflected signal may be used for calibration purposes and the like (and may for example be associated with the nasal turbinates and choanae). Accordingly, the first peak or a first few peaks may be used to calibrate the overall signal, and e.g. to identify and take account of slippage in the cannula or the like or congestion in the nostrils, e.g. by identifying a reduction in the selected peak(s) and by adjusting the signal values accordingly. This may be useful in compensating the detected transmitted or reflected signal for poor coupling, variable attenuation in the nasal cavities and the like.

It will be appreciated that when referring to transmitted and reflected detection signals, this generally refers to the dominant mechanism of the signal response, and that the detected signal may relate to the input signal as a complex combination of attenuation, transmission, refraction and reflection from various sites along the airway. Further, the detected signal may often be an indirect measurement, e.g. taken off-axis from the path of the sound signal and through the body of the patient, so that the sound signal is detected after it has passed through the relevant portion of the airway and coupled to the detector through the body tissue.

The present invention may also be used to determine other airway characteristics, and for example may provide information as to the resistance of the airway.

Thus, an experimental set-up is shown schematically in FIG. 23 in which an upper airway is modelled by a rubber tube 170 of 1.9 cm diameter. Pseudo-random noise of fixed amplitude was injected into one end of the tube 170 by an acoustic driver 171, and noise reaching the other end of the tube 170 was measured with an electret microphone 172 to provide a resultant sound pressure level (SPL). The driver and microphone are connected to the tube 170 by ports 173,174. The microphone output was monitored during a step-wise occlusion of the tube 170 at a constriction site F, whilst an airflow was generated by setting a level of CPAP (4 cm $H_2O$ or 10 cm $H_2O$).

Airflow ($\dot{V}$) was measured using a mass airflow meter (not shown), and the pressure drop ($\Delta P$) across the occlusion site F was also measured using pressure transducers 175,176. Resistance was then measured as the ratio of pressure drop to airflow.

Patency was determined as the ratio of the SPL of the constricted tube to the SPL of the open tube (as derived from the impulse response).

Patency was found to relate linearly to the log of resistance, as shown in FIG. 24 and in a curvilinear manner to cross-sectional area of the tube 170 at the point of restriction, as shown in FIG. 25, calculated on the assumption that the cross-section is approximated by an ellipsoid. It is also noted that the relationships between patency and resistance and area were independent of the level of CPAP used in the study.

It is to be understood that various alterations, additions and/or modifications may be made to the parts previously described without departing from the ambit and the spirit of the present invention, and that, in the light of the above teachings, the present invention may be implemented in a variety of manners as would be understood by the skilled person.

Australian and New Zealand Neonatal Network. Annual Report, 1996-1997.

Baumer J H. International randomised controlled trial of patient triggered ventilation in neonatal respiratory distress syndrome. Arch Dis Child 82: F5-F10, 2000.

Bernstein G, Mannino F L, Heldt G P, Callahan J D, Bull D H, Sola A, Ariagno R L, Hoffman G L, Frantz I D 3$^{rd}$, Troche B I, Roberts J L, Dela Cruz T V, and Costa E. Randomized multicenter trial comparing synchronized and conventional intermittent mandatory ventilation in neonates. J Pediatr 128: 453-63, 1996.

Dreyfuss D, Basset G, Soler P and Saumon G. Intermittent positive-pressure hyperventilation with high inflation pressures produces pulmonary microvascular injury in rats. Am Rev Resp Dis 132: 880-884, 1985.

Fahy, F. (1985) Sound and Structural Vibration. Radiation, Transmission and Response. London: Academic Press.

Froese A B. Role of lung volume in lung injury: HFO in the atelectasis-prone lung. Acta Anaesthesiol Scand Suppl 90:126-130, 1989.

Froese A B. High frequency oscillatory ventilation for adult respiratory distress syndrome: Let's get it right this time! Crit Cae Med 25: 906-908, 1997

Gerstmann D R, Minton S D, Stoddard R A, Meredith K S, Monaco F, Bertrand J M, Battisti O, Langhendries J P, Francois A and Clark R H. The Provo multicenter early high-frequency oscillatory ventilation trial: improved pulmonary and clinical outcome in respiratory distress syndrome Pediatrics. 98: 1044-1057, 1996.

Goncharoff, V., Jacobs, J E, and Cugell, D W Wideband acoustic transmission of human lungs. *Med. Biol. Eng. Comp.* 27:513-519, 1989.

HIFI Study Group. High frequency oscillatory ventilation compared with conventional mechanical ventilation in the management of respiratory failure in preterm infants. N Engl J Med 320: 88-93, 1989.

Jobe A. Pulmonary surfactant therapy. N Engl J Med 328: 861-864, 1993.

Kraman, S. S. Speed of low-frequency sound through lungs of normal men. J. Appl. Physiol. 55:1862-1867, 1983.

Lowe R D and Robinson B F. A physiological approach to clinical methods. Churchill, London, 1970.

McCulloch, P R, Forkert P G and Froese A B. Lung volume maintenance prevents lung injury during high-frequency oscillatory ventilation in surfactant-deficient rabbits. Am Rev Respir Dis 137: 1185-1192, 1988.

Northway H Q, Rosen R C and Porter D Y. Pulmonary disease following respiratory therapy of hyaline membrane disease. N Engl J Med 276: 357-368, 1967.

Rice, D. A. (1983) Sound speed in pulmonary parenchyma. J. Appl. Physiol. 54:304-308.

Rife D D & Vanderkooy J. Transfer function measurement with maximum length sequences. J Audio Eng Soc 37: 419-444, 1989.

Sheridan, B (2000) Acoustic evaluation of lung inflation in the preterm infant. B. Med. Sci. Thesis, RCBHR, Monash University.

Taghizadeh A & Reynolds EOR. Pathogenesis of bronchopulmonary dysplasia following hyaline membrane disease. Am J Pathol 82: 241-264, 1976.

Wodicka, G. R. and Shannon, D. C. Transfer function of sound transmission in subglottal human respiratory system at low frequencies. *J. Appl. Physiol.* 69(6):2126-2130, 1990.

Wodicka G R, Stevens, K N, Golub, H L, Cravalho, E G and Shannon, D. C. A model of acoustic transmission in the respiratory system. IEEE Ttrans Biomed. Eng. 36: 925-934, 1989.

The invention claimed is:

1. Apparatus for monitoring airway patency, the apparatus including:
   a sound generator for applying a sound signal in the audible frequency spectrum to an airway;
   a detector for detecting the sound signal after it has traveled through at least a portion of the airway; and
   an analyser for monitoring airway patency based on variations in the detected sound signal, wherein the analyser determines patency based on a variation in the profile of a response signal determined from said detected signal and compares characteristics of the response signal in at least two regions to determine patency.

2. Apparatus according to claim 1, wherein the airway may include one or more of: the buccal cavity, the nasal cavity, the pharyngeal region, the laryngeal region and the tracheal region.

3. The apparatus of claim 1, wherein the detector detects sound transmitted through said airway portion.

4. The apparatus of claim 1, wherein the detector detects sound reflected back from said airway portion.

5. The apparatus of claim 1, wherein the sound signal is applied through one or more of the following: (a) one of the nares; (b) both of the nares; (c) the mouth; (d) the mouth and the nares.

6. The apparatus of claim 1, wherein the sound signal is applied through at least one of: (a) a face mask; (b) a nose mask; (c) a mouth mask; (d) a nasal plug; (e) a nasal cannula.

7. The apparatus of claim 1, wherein the sound signal is applied at least:
   (a) to one nares and detected from the other nares;
   (b) to both nares and detected from both;
   (c) orally and detected orally; or
   (d) to the nose and/or mouth and detected in the other or both.

8. The apparatus of claim 1, wherein the sound detector is adapted to be positioned on one or more of: the chest, back, abdomen or the region of the suprastemal notch.

9. The apparatus of claim 1, wherein the applied sound signal is based on pseudo-random noise.

10. The apparatus of claim 9, wherein the sound generator generates sound signals based on a repeating noise signal sequence, the length of the repeated sequence being such that the repetition is substantially unperceived by the subject whose airway is being monitored.

11. The apparatus of claim 1, wherein the sound generator generates sound signals based on a repeating noise signal sequence, and wherein the repeated sequence is divided into a plurality of signal packets to allow for processing of the detected signal at a rate higher than the repeated sequence length.

12. The apparatus of claim 1, wherein the analyser includes a correlator for performing a cross-correlation of the detected sound signal with a reference signal.

13. The apparatus of claim 1, wherein the analyser determines an impulse response.

14. The apparatus of claim 1, wherein the analyser determines a frequency response.

15. The apparatus of claim 1, wherein the analyser determines a response to a combination of the airway and the monitoring apparatus.

16. The apparatus of claim 1, wherein the analyser determines a peak value in a signal response to determine patency.

17. Apparatus according to claim 16, wherein the apparatus determines the position of a peak in an impulse response and monitors the strength of the impulse response at that point over time in order to determine patency.

18. Apparatus according to claim 16, wherein the apparatus tracks a peak in an impulse response over time, and monitors the strength of the peak in order to determine patency.

19. The apparatus of claim 1, wherein the analyser compares response characteristics of regions proximal and distal to an obstruction or partial obstruction to determine patency.

20. Apparatus according to claim 1, wherein the apparatus monitors an energy shift in the detected response signal.

21. Apparatus according to claim 3, wherein the applied sound signal comprises frequencies according to one or more of the following:
    (a) frequencies between about 100 Hz and about 2,000 Hz;
    (b) frequencies between about 100 Hz and about 10,000 Hz;
    (c) frequencies between about 500 Hz and about 1500 Hz; and
    (d) frequencies between about 500 Hz and about 800 Hz.

22. Apparatus according to claim 1, wherein the applied sound signal has a frequency bandwidth that substantially prevents the perception of an unpleasant tonal quality in the applied sound signal.

23. Apparatus according to claim 1, wherein the sound generator is adapted to apply a sound signal based on one or more of: (a) a frequency characteristic of the patient airway; and (b) a resonant frequency of the airway that is substantially stable during open and closed mouth events.

24. Apparatus according to claim 1, including a tuner control for determining frequency characteristics for the applied sound signal that provide an optimum response signal.

25. Apparatus according to claim 1, wherein the analyser is adapted to monitor the signal level of the detected signal and for rejecting signal data above a threshold value.

26. Apparatus according to claim 25, wherein when signal data is rejected, the apparatus outputs patency data based on previous patency data.

27. Apparatus according to claim 25, wherein the analyser is adapted to divide the detected sound signal into a plurality of data packets, each packet being used to determine a patency value, and wherein when a packet includes sampled data above a threshold value, the data from the packet is rejected.

28. Apparatus according to claim 25, wherein the analyser is adapted to divide the detected sound signal into a plurality of packets, each packet being used to determine a patency value and each including a number of data samples of the detected sound signal, and wherein when a value of a detected data sample of a packet is above a threshold value, the detected data sample is adjusted to a lower value.

29. Apparatus according to claim 28, wherein the analyser is adapted to adjust a patency value based on an adjusted data packet value to compensate for said adjustment to said data packet value.

30. Apparatus according to claim 1, wherein the analyser is adapted to determine the fast Fourier transform of the detected sound signal and for attenuating frequency components that exceed a threshold value.

31. Apparatus according to claim 1, wherein the analyser determines the location of an obstruction based on the detected sound signal.

32. Apparatus according to claim 31, wherein the analyser determines an obstruction position based on a comparison of at least two portions of the response signal.

33. Apparatus according to claim 1, including a sensor for determining airflow in the airway.

34. Apparatus according to claim 33, wherein the analyser discriminates between a central breathing event and an obstructive breathing event based on patency and airflow measurements.

35. Apparatus according to claim 1, wherein the analyser discriminates between an apneic event and a hypopneic event based on the degree of patency of the airway.

36. Apparatus according to claim 1, wherein the analyser determines one or more of the following:
    (a) an obstruction when patency is low;
    (b) a partial obstruction when patency is reduced;
    (c) an obstruction when patency is low and airflow has ceased;
    (d) a partial obstruction when patency and airflow are reduced;
    (e) a cessation or reduction of an obstruction when patency rises;
    (f) a central apnea when patency is high and airflow has ceased;
    (g) an obstructive apnea when patency is low and airflow is reduced;
    (h) a central hypopnea when patency remains constant and airflow has ceased;
    (i) an obstructive hypopnea when patency and airflow are reduced.

37. Apparatus according to claim 1, wherein the analyser issues an alarm when patency is below a threshold value.

38. Apparatus for the monitoring of sleep-disordered breathing, the monitoring apparatus including patency monitoring apparatus according to claim 1, wherein the monitoring apparatus is adapted to perform determination of sleep-disordered breathing of a subject based on detected patency of the subject's airway, monitored during sleep.

39. Apparatus for providing a sleep-disordered breathing index, including patency apparatus according to claim 1 and including an index calculator for counting the number of breathing events that occur in a set time period based on at least the detected patency of the airway.

40. Patency apparatus according to claim 1, in combination with respiratory assist apparatus, wherein operation of the respiratory assist apparatus is controlled, at least in part, based on airway patency detected using the patency apparatus.

41. Patency apparatus according to claim 1, in combination with positive airway pressure apparatus, wherein a level of positive airway pressure applied to the patient by the positive airway pressure apparatus is controlled, at least in part, based on airway patency detected using the patency apparatus.

42. Patency apparatus according to claim 1, adapted to determine airway resistance based on airway patency.

43. Apparatus for determining airway resistance, the apparatus including:
- a sound generator for applying a sound signal in the audible frequency spectrum to an airway;
- a detector for detecting a response to the applied sound signal; and
- an analyser for determining airway resistance based on the detected response wherein the analyser determines airway resistance based on a variation in the profile of a response signal determined from said detected signal and compares characteristics of the response signal in at least two regions to determine airway resistance.

44. Apparatus for monitoring airway patency, the apparatus including:
- a sound generator for applying a sound signal in the audible frequency spectrum to at least a portion of an airway, the airway portion having an end proximal to the sound generator and an end distal from the sound generator;
- a detector for detecting a resulting sound signal at said distal end of said airway portion; and
- an analyser for determining patency for the airway portion based on the detected signal, wherein the analyser determines patency based on a variation in the profile of a response signal determined from said detected resulting sound signal and compares characteristics of the response signal in at least two regions to determine patency.

45. Apparatus for monitoring airway patency, the apparatus including:
- a sound generator for applying a sound signal in the audible frequency spectrum to at least a portion of an airway, the airway portion having an end proximal to the sound generator and an end distal from the sound generator;
- a detector for detecting a resulting sound signal at said proximal end of said airway portion, said sound signal including components of said applied sound signal that are reflected back to said proximal end of said airway; and
- an analyser for determining patency for the airway portion based on the detected signal, wherein the analyser determines patency based on a variation in the profile of a response signal determined from said detected signal and compares characteristics of the response signal in at least two regions to determine patency.

46. Apparatus for monitoring a state of an airway, the apparatus including:
- a sound generator for applying a sound signal in the audible frequency spectrum to an airway;
- a detector for detecting the sound signal after it has travelled through at least a portion of the airway; and
- an analyser for monitoring the state of the airway based on variations in the detected sound signal wherein the analyser determines the state of the airway based on a variation in the profile of a response signal determined from said detected signal and compares characteristics of the response signal in at least two regions.

47. An apparatus for determining characteristics of biological tissues, the apparatus including:
- a sound generating device which generates a sound;
- a recording device which records the sound after it has travelled from one position of the biological tissue, through the tissue and to another position of the tissue; and
- an analysis device which determines characteristics of the sound that has travelled through the tissue, wherein the analysis device determines the characteristics of the biological tissues based on a variation in the profile of a response signal determined from said detected signal and compares characteristics of the response signal in at least two regions to determine the characteristics of the biological tissues.

* * * * *